US010413706B2

(12) United States Patent
Amisar et al.

(10) Patent No.: US 10,413,706 B2
(45) Date of Patent: Sep. 17, 2019

(54) METHOD AND APPARATUS FOR INSERTING A CATHETER TUBE

(71) Applicant: BULLPUP SCIENTIFIC LTD., Haifa (IL)

(72) Inventors: Shai Amisar, Tel Aviv (IL); Ronen Radomski, Haifa (IL)

(73) Assignee: BULLPUP SCIENTIFIC LTD., Haifa (IL)

( * ) Notice: Subject to any disclaimer, the term of this patent is extended or adjusted under 35 U.S.C. 154(b) by 186 days.

(21) Appl. No.: 15/501,544

(22) PCT Filed: Aug. 5, 2015

(86) PCT No.: PCT/IL2015/050804
§ 371 (c)(1),
(2) Date: Feb. 3, 2017

(87) PCT Pub. No.: WO2016/020923
PCT Pub. Date: Feb. 11, 2016

(65) Prior Publication Data
US 2017/0224961 A1  Aug. 10, 2017

Related U.S. Application Data

(60) Provisional application No. 62/033,134, filed on Aug. 5, 2014.

(51) Int. Cl.
*A61M 25/06* (2006.01)
*A61M 25/00* (2006.01)
*A61M 39/10* (2006.01)
*A61M 39/24* (2006.01)

(52) U.S. Cl.
CPC .... *A61M 25/0606* (2013.01); *A61M 25/0097* (2013.01); *A61M 25/0618* (2013.01); *A61M 39/10* (2013.01); *A61M 39/24* (2013.01)

(58) Field of Classification Search
CPC .............. A61M 25/0606; A61M 25/02; A61M 25/0637; A61M 25/0612; A61M 25/0613
See application file for complete search history.

(56) References Cited

U.S. PATENT DOCUMENTS

| 4,209,015 A | 6/1980 | Wicks |
| 4,231,367 A | 11/1980 | Rash |
| 4,496,348 A | 1/1985 | Genese et al. |

(Continued)

FOREIGN PATENT DOCUMENTS

| EP | 1 437 155 | 7/2004 |
| EP | 1 661 598 | 5/2006 |

(Continued)

OTHER PUBLICATIONS

Search Resort issued in EP Appln. No. 15829314.2 dated Aug. 21, 2018.

Primary Examiner — Laura A Bouchelle
(74) Attorney, Agent, or Firm — Nixon & Vanderhye P.C.

(57) ABSTRACT

The present invention relates to a catheter insertion system and method. The system comprises an IV catheter comprising a distal cannula attached to a proximal hollow hub; a forward arm attachably connected to a proximal portion of said IV catheter or element connected thereto, and extending distally therefrom; and a needle configured to pass through and protrude from the cannula.

14 Claims, 32 Drawing Sheets

(56) References Cited

U.S. PATENT DOCUMENTS

| | | | |
|---|---|---|---|
| 4,500,312 A | | 2/1985 | McFarlane |
| 4,629,450 A | * | 12/1986 | Suzuki ............. A61M 25/0606 |
| | | | 604/104 |
| 5,192,273 A | | 3/1993 | Bierman et al. |
| 5,512,052 A | | 4/1996 | Jesch |
| 5,674,201 A | | 10/1997 | Steinman |
| 5,738,660 A | * | 4/1998 | Luther ................. A61M 5/322 |
| | | | 604/164.08 |
| 5,944,695 A | | 8/1999 | Johnson et al. |
| 7,291,128 B2 | | 11/2007 | Rossi et al. |
| 8,337,461 B2 | * | 12/2012 | Burkholz .......... A61M 25/0637 |
| | | | 604/164.01 |
| 2004/0122373 A1 | | 6/2004 | Botich et al. |
| 2006/0265042 A1 | | 11/2006 | Catanese, III et al. |
| 2007/0282268 A1 | * | 12/2007 | Mayse ............. A61M 39/0606 |
| | | | 604/164.01 |
| 2011/0224617 A1 | | 9/2011 | Miner |
| 2012/0210569 A1 | | 8/2012 | Schmitt |
| 2012/0277679 A1 | | 11/2012 | Steube |
| 2013/0023826 A1 | | 1/2013 | Ishida |

FOREIGN PATENT DOCUMENTS

| | | |
|---|---|---|
| EP | 1 752 188 | 2/2007 |
| EP | 2 157 997 | 3/2010 |
| EP | 2 606 929 | 6/2013 |
| WO | WO 2008/147600 | 12/2008 |

* cited by examiner

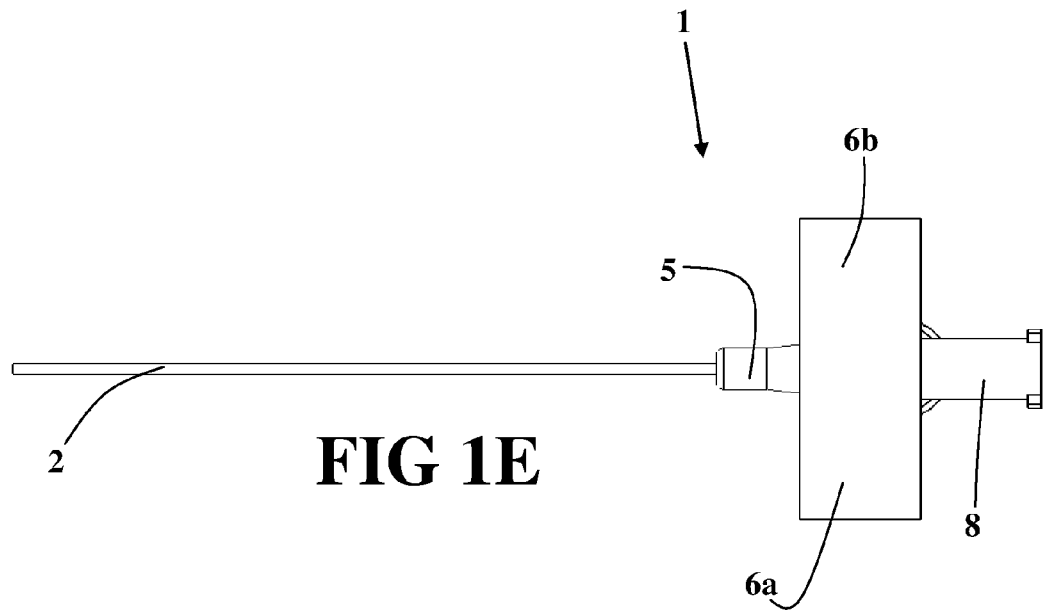
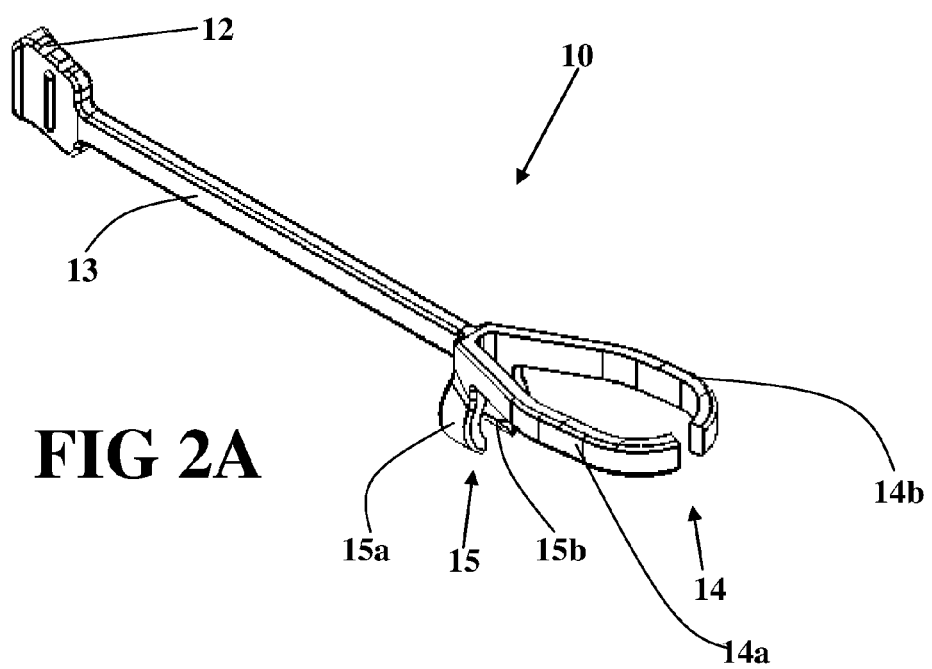

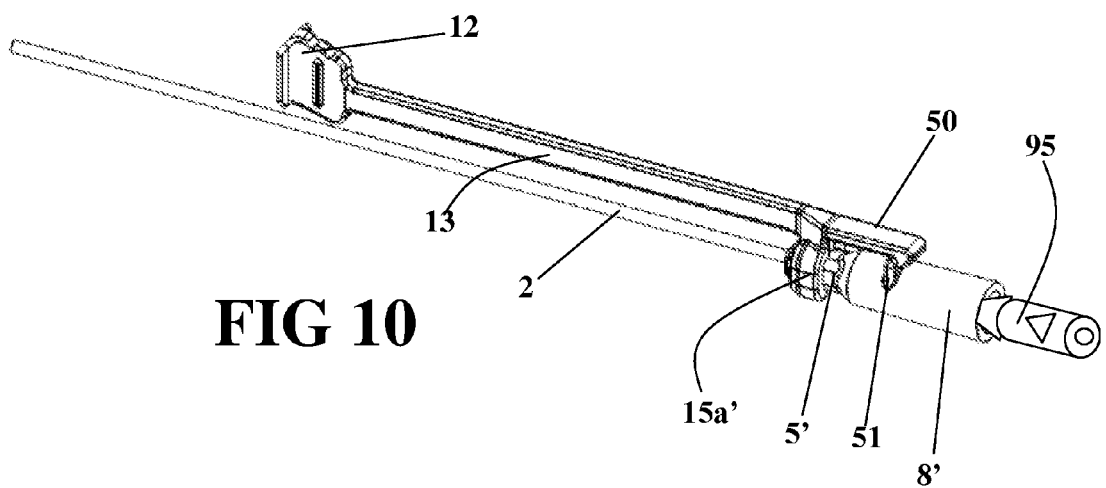

METHOD AND APPARATUS FOR INSERTING A CATHETER TUBE

This application is the U.S. national phase of International Application No. PCT/IL2015/050804 filed 5 Aug. 2015, which designated the U.S. and claims the benefit of U.S. Provisional Application No. 62/033,134, filed 5 Aug. 2014, the entire contents of each of which are hereby incorporated by reference.

FIELD OF THE INVENTION

The present invention relates to intravascular catheter devices. More particularly, the invention relates to methods and apparatuses for facilitating the insertion of an IV catheter.

BACKGROUND OF THE INVENTION

It is known in the art to provide peripheral intravenous therapy using a catheter having a cannula or catheter tube to provide access into subcutaneous veins thereby to introduce medication, drugs, chemotherapy, nutrition and various other fluids into a vein of a subject. The present procedure includes inserting a hypodermic needle together with a catheter having an in-dwelling cannula into a suitable vein, withdrawing the needle and leaving the in-dwelling cannula in the vein. Such a catheter is typically provided with a suitable closure and various adapter mechanisms to enable the aseptic introduction of fluid medicaments from a hypodermic syringe or from an intravenous drip.

Inserting a cannula into the intravenous system can be difficult and is prone to complications. Skilled medical personnel must puncture the skin correctly at a correct location and insert the cannula in a correct blood vessel. Between the puncturing stage and the insertion stage the medical personnel must have the skill to hold the catheter insertion system in place prior to the insertion. Many times, the medical personnel accidently "pulls out" and loses the spot point of the required insertion location leading to another puncturing attempt. This causes unnecessary pain and discomfort for the patient and unnecessary additional stress for the medical personnel, along with unnecessary efforts of additional attempts.

It has been proven that an insertion of a longer cannula, 7-10 cm, especially if it is made from softening polyurethane, reduces complications associated with short catheters and reduces the appearance of phlebitis. However, long catheters are difficult to insert as the grip is quite far from the insertion site, a fact that reduces the stability of the operator and makes the insertion of a catheter to the vein even more difficult.

The Powerglide Midline Catheter 2012 IFU of C.R. Bard Inc., provides a solution for the reduction of complicated insertions. It comprises a catheter insertion system comprising a guidewire. When punctured into a blood vessel, a guidewire is initially inserted into the blood vessel. Afterwards, the medical personnel can calmly arrange the next steps of the procedure because the guidewire is already in the desired blood vessel and there is no threat of an early pull out. Then the catheter tube is inserted distally along the guidewire.

A considerable disadvantage of the prior art catheter device stems from the requirement to needlessly initially insert a guidewire to prevent an early pullout and loss of the desired blood vessel insertion location.

U.S. Pat. No. 5,512,052 relates to catheterization set for placing a catheter in a blood vessel, comprising a puncture needle with a needle hub carrying a grip device, a catheter surrounding the puncture needle and having a catheter hub.

U.S. Pat. No. 7,291,128 relates to a sheath with a stationary deflector disposed on the path of the slider so that contact between the slider and the deflector causes the slider to be inclined and consequently causes the needle to be inclined inside the sheath.

EP 1437155 relates to a catheter with a needle and a cannula for the introduction thereof by means of only one hand into the blood conduits of a living being's body.

U.S. Pat. No. 4,231,367 relates to an infusion catheter assembly, which includes a catheter unit and an insertion needle unit, provided with fins extending from the head of the insertion needle unit. The fins may be gripped by the fingers and pivoted inward to firmly engage the catheter unit during insertion of the catheter unit into a vein.

The prior art devices do not provide sufficient means for a suitable insertion.

It is therefore an object of the present invention to provide methods and means for the controlled, safe aseptic insertion of an intravascular catheter tube into a peripheral blood vessel.

It is another object of the present invention to provide an intravascular catheter insertion system comprising means for preventing accidental withdrawal of the catheter system.

It is another object of the present invention to provide intravascular catheter insertion system which allows stabilizing the inserting hand and sliding the catheter over the needle with the second hand.

It is another object of the present invention to provide an intravascular catheter insertion system which provides a forward griping point for catheters over 5 cm.

It is a further object of the present invention to provide an intravascular catheter insertion system without the need of a guidewire or other guiding means.

Other objects and advantages of the invention will become apparent as the description proceeds.

SUMMARY OF THE INVENTION

The present invention provides a catheter insertion system that may be used for the controlled, aseptic insertion of catheters and similar indwelling tubular elements into the vasculature by means of the transcutaneous route.

The present invention relates to a system comprising an IV catheter with a forward arm attachably connected to the IV catheter proximal hub and extending distally therefrom (preferably substantially) parallel to the IV catheter distal cannula. The system comprises a puncturing needle passed through the IV catheter. Two protecting gripping arms (graspable arms) for the medical personnel are attached on the proximal portion of the system and extend distally. During insertion, the puncturing needle punctures a blood vessel. The forward arm is pulled distally pulling the parallel cannula distally. Once the cannula is sufficiently inserted in the blood vessel the protecting gripping arms and the needle are proximally extracted, taken out and disposed of.

The present invention also relates to a method for insertion of the present invention device.

It should be noted that the term "proximal" is used herein to refer to elements of the catheter device which are located in relative proximity to the operator, and the term, "distal" is used herein to refer to elements of the catheter device the location of which is relatively distant from the operator.

The present invention relates to a method and system comprising a catheter with a distal cannula/sheath and with a forward arm attached to the proximal part of the catheter and extending distally therefrom. The motion of the cannula is set by the motion of the forward arm attached thereto. As opposed to prior art cannulas which grasping means are approached to from the proximal end of the cannula, the present invention enables grasping means from a location above the cannula and even above and distally from the distal end of the cannula. This feature is advantageous as it enables the medical personnel user to grasp and maneuver the cannula from a more comfortable location. This also reduces the hazard of early pull-outs that occur in many prior art cases due to a more complex and uncomfortable approach to the cannula from the proximal direction. The present invention enables a needle puncture (needle passing through and protruding from within the cannula) and the cannula insertion immediately thereafter, thus substantially increasing the chance for a successful insertion. Even a partial distal movement of the cannula immediately after the puncture is advantageous due to the fact that once the cannula is even just partially in the blood vessel, the danger of an early pullout ceases to exist, and the cannula can be fully inserted at ease, slowly and safely, without pressure.

The present invention is especially advantageous when used with long catheters (e.g. longer than 7 cm) enabling improvement of the stability of the operator by providing a forward arm grasping means for maneuvering the catheter during insertion. Thus instead of maneuvering the catheter and needle from a far proximal unstable location (with high percentages of pull outs), the catheter is maneuvered from a distal, comfortable and stable location.

After the cannula is partially, or fully inserted in place, the forward arm is disconnected from the catheter, the needle is proximally removed, and the catheter is fixed to the patient.

The present invention (for the purpose of illustration) provides a "U" shaped structure (the "U" being on its side) thus the user uses the upper arm of the "U" (forward arm handle) to maneuver and insert the lower arm of the "U" (cannula) into the body.

The present invention comprises a needle holder unit (or a catheter closing unit) that protects and stabilize the cannula and can be grasped by the user thus enabling a stable use of the system with all its connected components. This enables a stable insertion comprising the needle (passing through within the cannula and protruding therefrom) puncturing, and the distal maneuvering of the cannula. The grasping means (either the needle holder unit or the catheter closing unit) are easily proximally removed after insertion and the catheter is fixed to the patient.

The present invention relates to a catheter insertion system comprising:
a. an IV catheter comprising a distal cannula attached to a proximal hollow hub;
b. a forward arm attachably connected to a proximal portion of said IV catheter or element connected thereto, and extending distally therefrom;
c. a needle configured to pass through and protrude from the cannula.

Preferably, the IV catheter comprises two or more side wings.

Preferably, the IV catheter comprises a proximal valve.

Preferably, the IV catheter comprises a proximal hollow end portion which allows connection to an intravenous infusion line and capping.

Preferably, the forward arm comprises a distal forward grip.

Preferably, the forward arm comprises a middle section connecting between the distal forward grip and a proximal grip, wherein the proximal grip comprises two arms extending proximally and substantially curved adapted to connect around the valve.

Preferably, the forward arm comprises a middle section connecting between the distal forward grip and a downward grip connected to the proximal end of said middle section, wherein said downward grip comprises two grasping arms extending downwards and substantially curved.

Preferably, the the downward grip is a snap-on clip.

Preferably, the forward arm is attachably connected to the IV catheter proximal hollow hub by means of the downward grip thus fixing said forward arm to said proximal hollow hub.

Preferably, the forward arm is substantially parallel to the cannula.

Preferably, the forward arm comprises a proximal liftable gripper; and the IV catheter comprises a proximal hollow end portion comprising a flat protrusion,
wherein the proximal liftable gripper comprises a proximal protrusion extending downwards with a distal flat portion adapted to grip and be placed at the proximal side of said flat protrusion.

Preferably, the forward arm comprises flexible material.

Preferably, the middle section comprises a distal portion connected to the forward grip and a thinner proximal portion connected to the downward grip, wherein the thinner proximal portion is flexible.

Preferably, the system further comprises a needle holder unit comprising the needle and two side arms substantially parallel to said needle.

Preferably, the needle holder unit comprises a proximal hub, wherein the needle is distally connected to said proximal hub.

Preferably, the needle holder unit further comprises two side arms connected to the proximal hub at their proximal ends.

Preferably, the two side arms comprise slanted portions at their distal ends, such that said distal ends are disposed near to each other.

Preferably, the portions of the two side arms proximal to the slanted portions are generally straight and parallel to the needle.

Preferably, the slanted portions are connected to forward finger grips at their distal ends.

Preferably, the forward finger grips are substantially parallel to each other and to the needle.

Preferably, the forward finger grips comprise inner notch portions with half circular inner portions forming a hollow passage configured for the needle to pass therethrough.

Preferably, the forward finger grips are configured to hold and/or secure the middle section therebetween.

Preferably, a portion of the needle holder unit proximal hub is configured to pass through and be fixed to the inner hollow portion of the hollow end portion.

Preferably, the middle section comprises two curved flaps that extend outwardly and proximally from the distal end of said middle section.

Preferably, the distal edges of the forward finger grips each comprise a notch on their distal outer side, wherein said notches are configured to receive the flaps.

Preferably, the IV catheter comprises a proximal hollow end portion; and wherein the system further comprises a safety capsule, wherein the needle is freely slidable in relation to said safety capsule, wherein said safety capsule automatically senses the end of the needle and instantly locks out to fully encapsulate the distal needle tip of the needle, wherein said safety capsule is proximally attached to the proximal hollow end portion in a luer connection.

Preferably, the forward arm is attachably connected to the safety capsule by means of the downward grip thus fixing said forward arm to said safety capsule.

Preferably, the IV catheter comprises a proximal hollow end portion; and wherein the system further comprises a one-way valve connected in a luer connection to the proximal end of the hollow end portion.

Preferably, the one-way valve is a duckbill valve or a casing comprising a duckbill valve.

Preferably, the forward arm is attachably connected to the casing comprising the duckbill valve by means of the downward grip thus fixing said forward arm to said casing.

Preferably, the cannula and needle passing therethrough, are in a position elevated in height from the height of the bottom of the side arms.

Preferably, the system comprises two grasping points:
a. a proximal grasping point, and
b. a distal grasping point;
wherein said grasping points are configured to perform maneuvering of the cannula.

Preferably, the side arms are configures to open outwardly when the catheter hub and/or downward grip engage the slanted portions.

The present invention relates to a catheter insertion system comprising:
a. an IV catheter with a distal cannula attached to a proximal hollow hub, and comprising a proximal hollow end portion;
b. a forward arm attachably connected to a proximal portion of said IV catheter or element connected thereto, and extending distally therefrom;
c. a catheter closing unit comprising a proximal stabilizing grip which comprises a hollow surface corresponding in shape and adapted to be close fitting around said proximal end portion;
said catheter closing unit further comprises two side arms attached to said proximal stabilizing grip.

Preferably, the two side arms comprise slanted portions at their distal ends, such that said distal ends are disposed near to each other.

Preferably, the portions of the two side arms proximal to the slanted portions are generally straight and parallel to each other.

Preferably, the slanted portions are connected to forward finger grips at their distal ends.

Preferably, the forward finger grips are substantially parallel to each other.

Preferably, the forward finger grips comprise inner notch portions with half circular inner portions forming a hollow passage configured for a needle to pass therethrough.

Preferably, the forward arm comprises a distal forward grip;
wherein the forward arm comprises a middle section connecting between the distal forward grip and a downward grip connected to the proximal end of said middle section,
wherein said downward grip comprises two grasping arms extending downwards and substantially curved;
wherein the forward finger grips are configured to hold and/or secure the middle section therebetween.

Preferably, the forward arm comprises a distal forward grip;
wherein the forward arm comprises a middle section connecting between the distal forward grip and a downward grip connected to the proximal end of said middle section,
wherein said downward grip comprises two grasping arms extending downwards and substantially curved;
wherein the middle section comprises two curved flaps that extend outwardly and proximally from the distal end of said middle section;
wherein the distal edges of the forward finger grips each comprise a notch on their distal outer side, wherein said notches are configured to receive the flaps.

Preferably, the system further comprising a stopper placed at a stop location on the proximal hollow end portion.

Preferably, the side arms comprise snaps near their proximal ends, wherein said snaps extend inwardly from the inner sides of said side arms, wherein said snaps each comprise two inwardly curved arms that are configured to snap on the IV catheter hub or proximal hollow end portion fixing said side arms thereto.

Preferably, the cannula is in a position elevated in height from the height of the bottom of the side arms.

Preferably, the system comprises two grasping points:
a. a proximal grasping point, and
b. a distal grasping point;
wherein said grasping points are configured to perform maneuvering of the cannula.

Preferably, the forward arm comprises a distal forward grip;
wherein the forward arm comprises a middle section connecting between the distal forward grip and a downward grip connected to the proximal end of said middle section,
wherein said downward grip comprises two grasping arms extending downwards and substantially curved;
wherein the side arms are configures to open outwardly when the catheter proximal hub and/or downward grip engage the slanted portions.

The present invention relates to a catheter insertion system comprising:
a. an IV catheter with a distal cannula attached to a proximal hollow hub, and comprising a proximal hollow end portion;
b. a forward arm attachably connected to a proximal portion of said IV catheter or element connected thereto, and extending distally therefrom;
c. a needle unit comprising a needle distally attached to a proximal hub, said needle unit (hub) optionally comprising a stopper;
d. a catheter closing unit comprising a proximal stabilizing grip which comprises a hollow surface corresponding in shape and adapted to be close fitting around said needle unit proximal hub;
said catheter closing unit further comprises two side arms attached to said proximal stabilizing grip;
wherein the needle unit hub distal portion is configured to connect in a luer connection to the proximal end of the proximal hollow end portion.

The present invention relates to a forward arm comprising a distal forward grip, a middle section connecting between the distal forward grip and a downward grip connected to the proximal end of said middle section, wherein said downward grip comprises two grasping arms extending downwards and substantially curved. Preferable embodiments of the forward arm of the present invention are described more in detail herein.

The present invention relates to a catheter insertion system comprising:
a. an IV catheter with a distal cannula attached to a proximal hollow hub;

b. a forward arm as described herein wherein the downward grip is configured to attach to the proximal hollow hub;

wherein preferable embodiments of this system of the present invention are described more in detail herein.

The present invention relates to a catheter closing unit comprising a proximal stabilizing grip which comprises a hollow surface corresponding in shape and adapted to be close fitting around a needle unit hub or a catheter hub or proximal end portion;

wherein said catheter closing unit comprises two side arms attached to said proximal stabilizing grip.

wherein the two side arms comprise slanted portions at their distal ends, such that said distal ends are disposed near to each other;

wherein the portions of the two side arms proximal to the slanted portions are generally straight and parallel to each other;

wherein the slanted portions are connected to forward finger grips at their distal ends;

wherein the forward finger grips are substantially parallel to each other. Preferable embodiments of the catheter closing unit of the present invention are described more in detail herein.

The present invention relates to methods of insertion of catheters and cannulas of the systems described herein.

The present invention relates to a method for inserting an IV catheter into a blood vessel of a patient comprising the steps of:
 A) providing a needle passing through said IV catheter, puncturing the patient's blood vessel;
 B) providing a forward arm attachably connected to a proximal portion of said IV catheter or element connected thereto and extending distally therefrom, pulling/pushing said forward arm distally thus inserting the cannula into the blood vessel;
 C) inserting the cannula in place by continuing to pull/push the forward arm distally (a "full" insertion i.e. until it is located in its intended position/location);
 D) proximally pulling the puncturing needle until it exits the IV catheter;
 E) disconnecting the forward arm from said IV catheter or element connected thereto;
 F) fixing the IV catheter to the patient's skin.

BRIEF DESCRIPTION OF THE DRAWINGS

The present invention is illustrated by way of example in the figures of the accompanying drawings, in which like references indicate similar elements and in which:

FIGS. 1A-1E illustrate perspective views of an embodiment of an IV catheter of the present invention at different angles.

FIGS. 2A-2D illustrate perspective views of the forward arm of the present invention at different angles.

FIG. 10 illustrates a perspective view of an embodiment relating to a casing comprising a duckbill valve.

DETAILED DESCRIPTION OF PREFERRED EMBODIMENTS

The present invention is primarily directed to a catheter insertion system comprising a device comprised of two main portions. One portion is an IV catheter comprising a hollow cannula suitable for insertion into a peripheral blood vessel, a hub portion and a forward handle. The other main portion comprises a needle connected to a hub. When the needle is inserted into the cannula all the way through wherein the needle extends beyond the cannula, the device is ready to be used on a patient.

The needle punctures the skin and is inserted with the cannula distal tip into the venous system. Typically, a flow of blood flows up the distal tip in the cannula indicating a correct positioning within the blood vessel. At this stage Prior Art devices require the medical personnel to then insert the cannula into the body by means of a grip located at the proximal end of a device, which sometimes leads to losing the forward grip of the device, what can cause a pullout of the cannula from the body. The present invention comprises a forward grip arm connected to the cannula that enables the insertion of the cannula into the body without further moving the inserting hand. This reduces the possibility of losing the vein by unintentionally allowing the tip of the catheter to move out of the hole in the vein prior to the insertion of the cannula.

The present invention is particularly useful when using a long IV catheter. In cases of long IV catheters the grip located at the proximal end of a device is located at an even more proximal location, what causes even more discomfort and loss of stability. Thus the chances of accidental pullout increase.

Figure 1A:
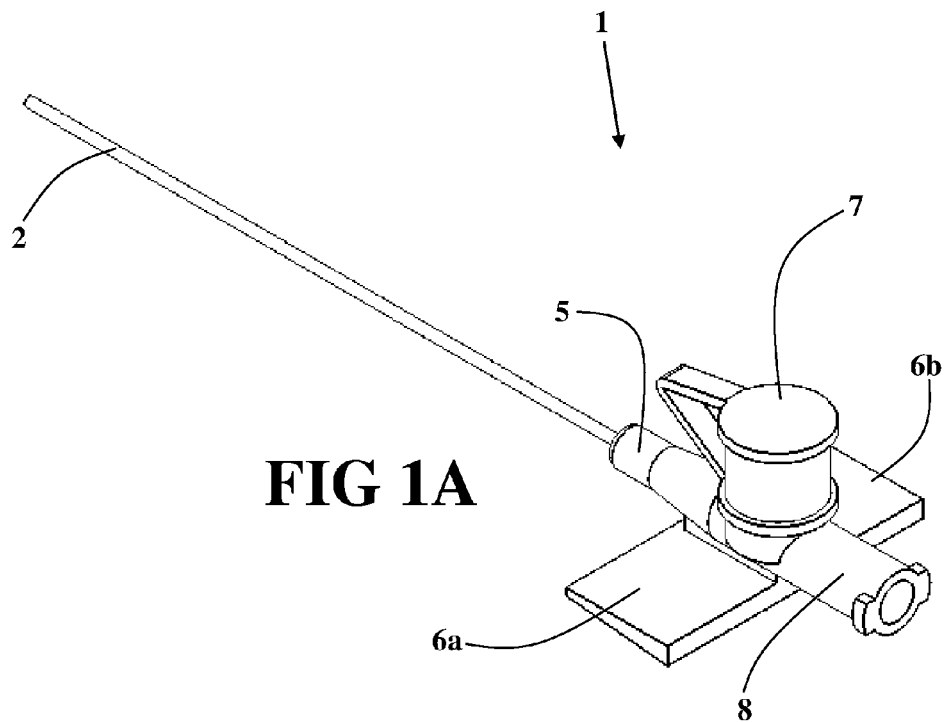

FIG. 1A shows a perspective view of an IV catheter 1 of the present invention. In this preferred embodiment the intravascular IV catheter 1 comprises a hollow cannula 2 and a proximal hollow hub 5 connected to the proximal end of the cannula 2. The IV catheter 1 (preferably) further comprises side wings 6a and 6b for manual handling and securing the catheter with adhesives and a proximal valve 7 to allow injection of drugs with a syringe. The IV catheter 1 further comprises a proximal hollow end portion 8 which allows connection to an intravenous infusion line, and capping in between uses. The hub 5 and end portion 8 are connected and continuously hollow (the hub 5 being distal to end portion 8) enabling the insertion of a needle therethrough, and through the cannula as will be explained herein.

Figure 1B:
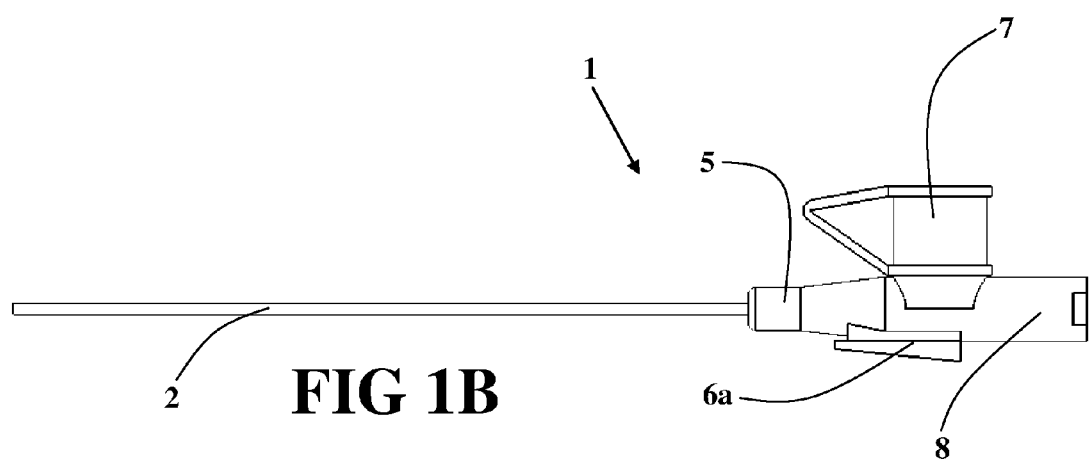
Figure 1C:
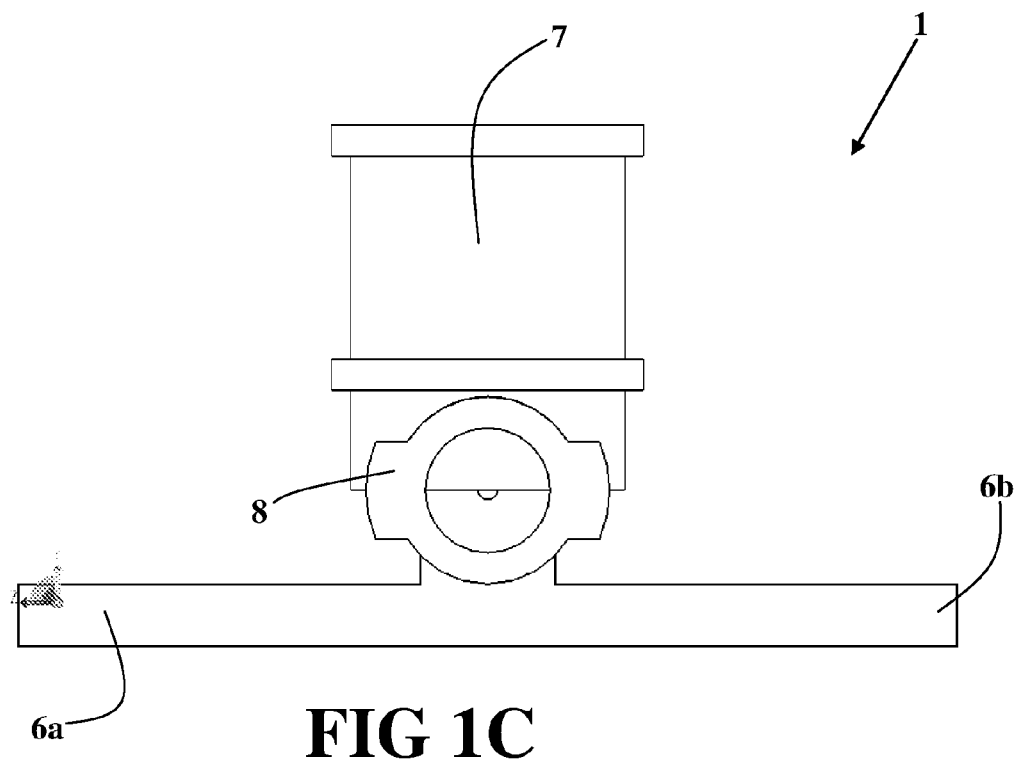
Figure 1D:
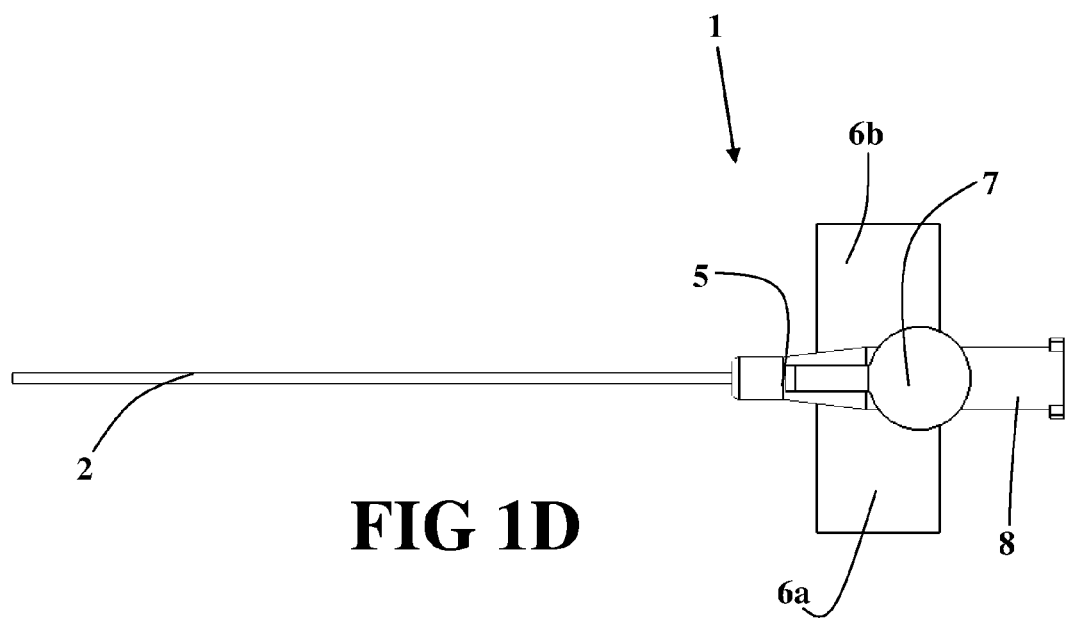

FIG. 1B shows a perspective side view of IV catheter 1 and FIG. 1C shows a perspective back view of it. FIG. 1D shows a perspective top view of IV catheter 1 and FIG. 1E shows a perspective bottom view of it.

According to an embodiment of the present invention the IV catheter is a standard IV catheter such as Introcan Safety® catheter of the B Braun company. According to an embodiment, the IV catheter (its structural elements) is made preferably from one or more of the following: polyurethane, PTFE, Polyethylene. The IV catheter cannula diameter is preferably between 0.5 mm to 2 mm, and length preferably between 4-15 cm, most preferably 8 cm. The sizes of the wings, hub, end portion and valve are such as in standard existing catheters.

The present invention comprises a forward arm 10 (FIG. 2A) adapted to be connected to the IV catheter 1. The forward arm 10 comprises a distal forward grip 12 for advancing the IV catheter 1 distally. The term "forward arm" and "forward handle" are used herein interchangeably.

According to an embodiment of the present invention, the forward arm 10 comprises a middle section 13 connecting between the distal forward grip 12 and a proximal grip 14. The proximal grip 14 comprises two arms 14a and 14b, extending proximally and substantially curved (inwards), adapted to connect around valve 7 and grip it, as shown in FIGS. 3A-3D.

According to an embodiment, the forward arm 10 comprises a downward grip 15 attached to the proximal end of middle section 13. The downward grip 15 comprises two grasping arms 15a and 15b extending downwards and substantially curved (inwards), adapted to connect around (and grip) hub 5 (preferably a snap-on tube clip connection wherein downward grip 15 snaps on hub 5), thus fixing forward arm 10 to the IV catheter 1 (at hub 5). The forward arm 10 can be easily disconnected from IV catheter 1 after the insertion of the IV catheter 1 by disengaging the arms of downward grip 15 from hub 5, and lifting the proximal grip 14 from around valve 7.

Figure 2B:
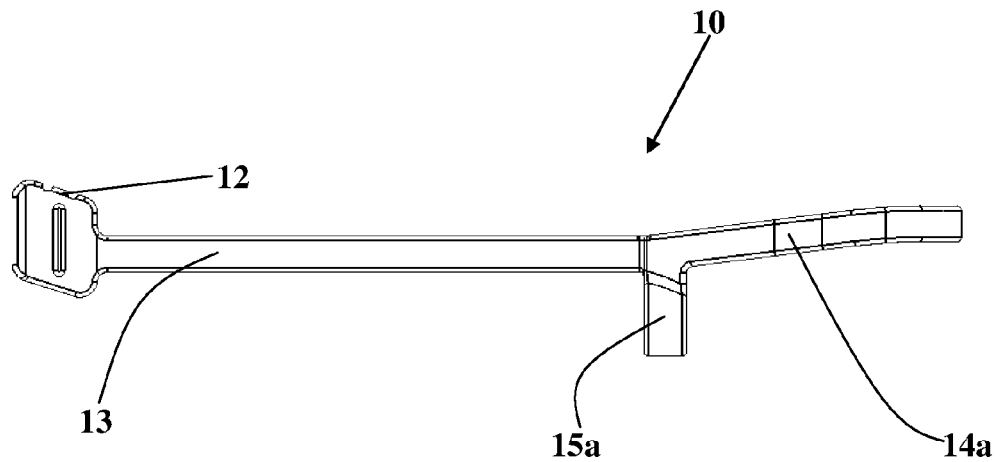
Figure 2C:
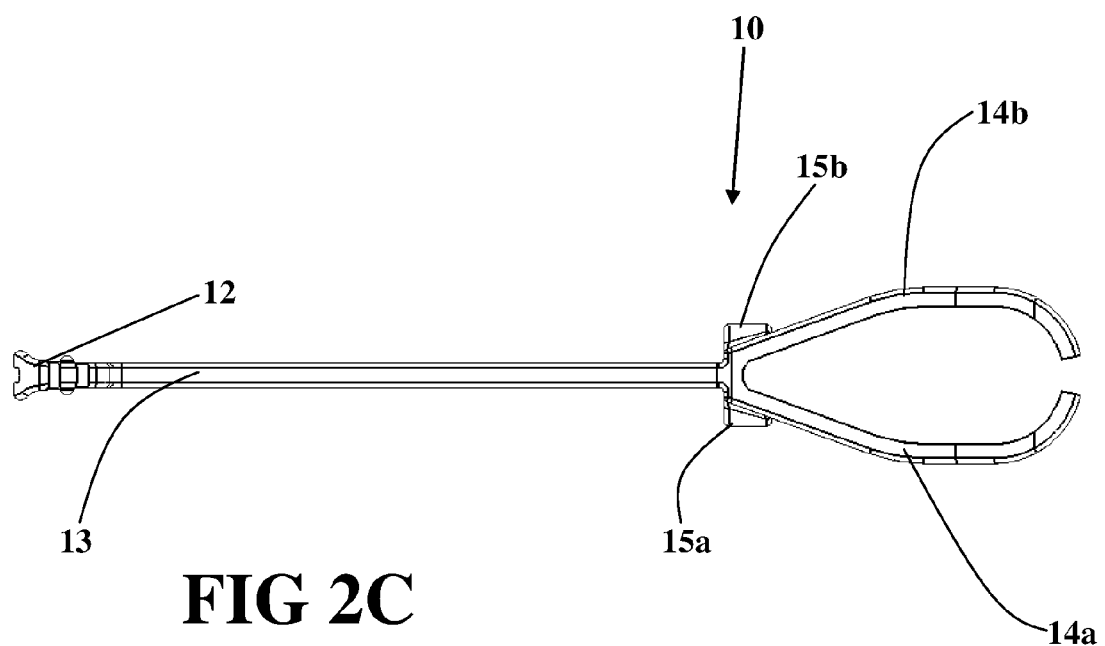
Figure 2D:
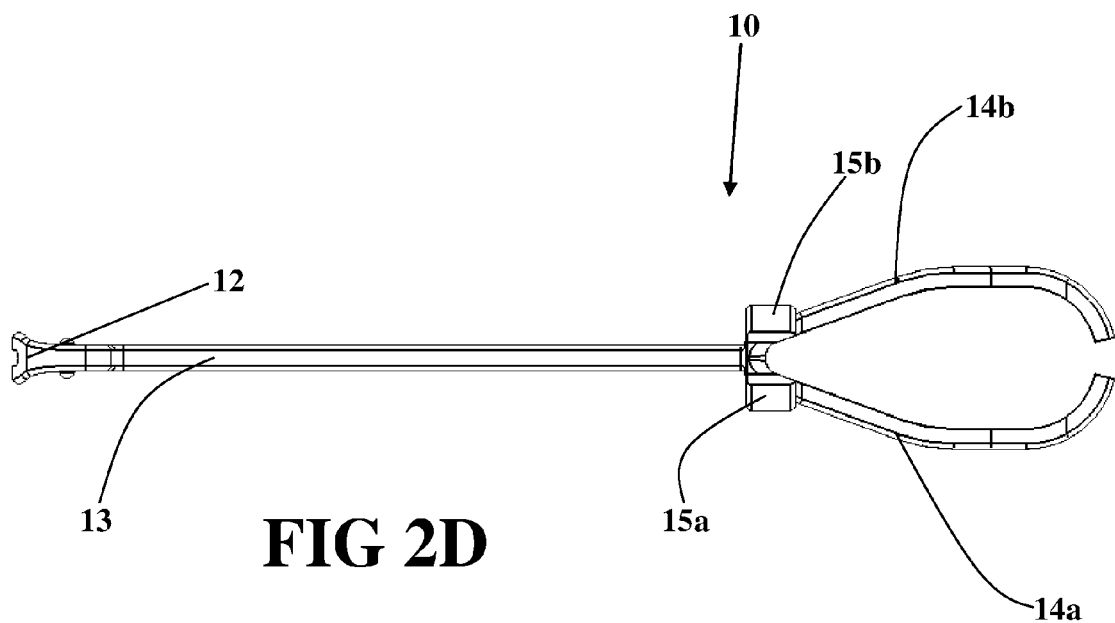

FIG. 2B shows a perspective side view of forward arm 10, FIG. 2C shows a perspective top view of it and FIG. 2D shows a perspective bottom view of it.

The forward arm 10 length is usually between 4 cm and 10 cm and preferably 7 cm. Its width is usually between 1.5 cm and 5 cm and preferably 2 cm. Its thickness is usually between 1 cm and 5 cm and preferably 1.5 cm.

The forward grip 12 length is usually between 5 mm and 15 mm and preferably 10 mm. Its width is usually between 1 mm and 10 mm and preferably 5 mm. Its thickness is usually between 1 mm and 4 mm and preferably 2 mm.

The middle section 13 length is usually between 2 cm and 8 cm and preferably 5 cm. Its width is usually between 1 mm and 5 mm and preferably 2 mm. Its thickness is usually between 1 mm and 5 mm and preferably 2 mm.

The arms 14a and 14b length is usually between 1 cm and 4 cm and preferably 1.5 cm. Their width is usually between 1 mm and 5 mm and preferably 2 mm. their thickness is usually between 1 mm and 3 mm and preferably 1.5 mm.

The arms 15a and 15b length is usually between 3 mm and 10 mm and preferably 7 mm. their width is usually between 2 mm and 6 mm and preferably 3 mm. their thickness is usually between 0.8 mm and 3 mm and preferably 1.5 mm.

Preferably, the cannula 2 extends 2-5 cm beyond the distal end portion of the forward grip 12.

Figure 3A:
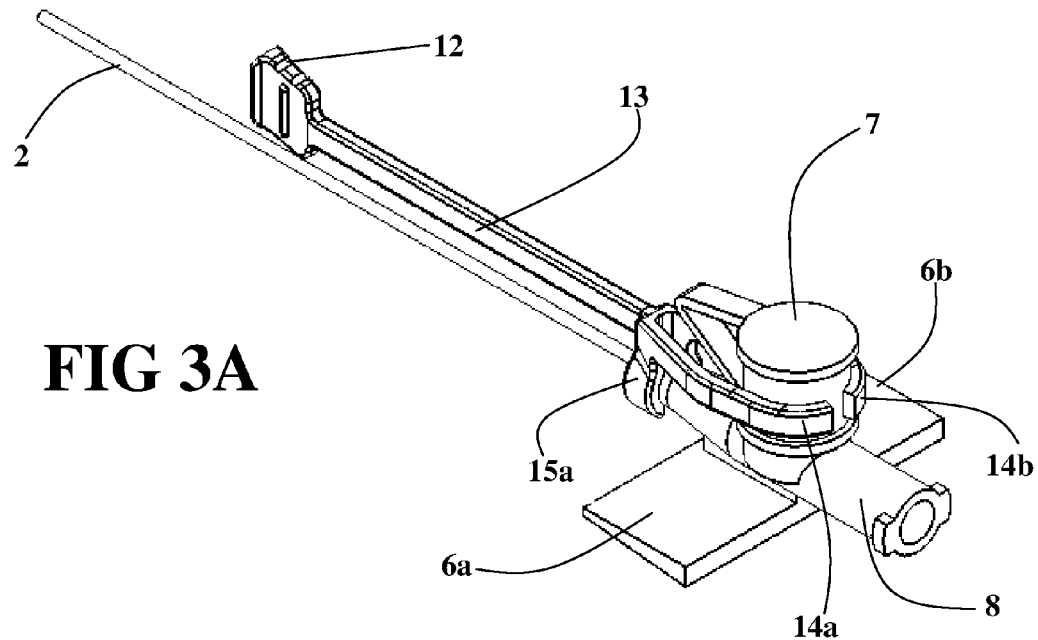
FIGS. 3A-3E illustrate perspective views of the forward arm fixed on the IV catheter, of the present invention at different angles.
Figure 3B:
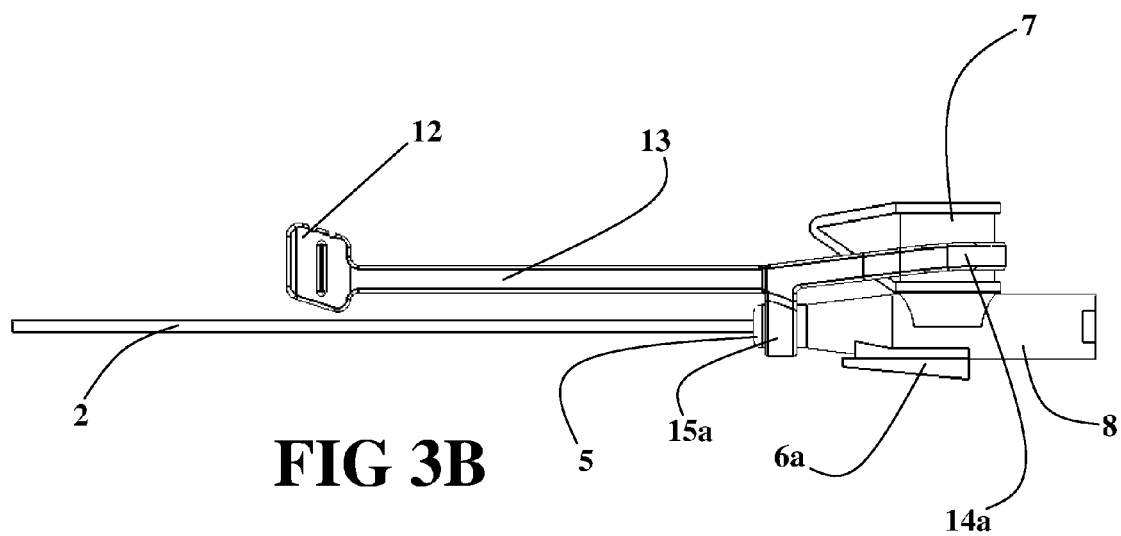
Figure 3C:
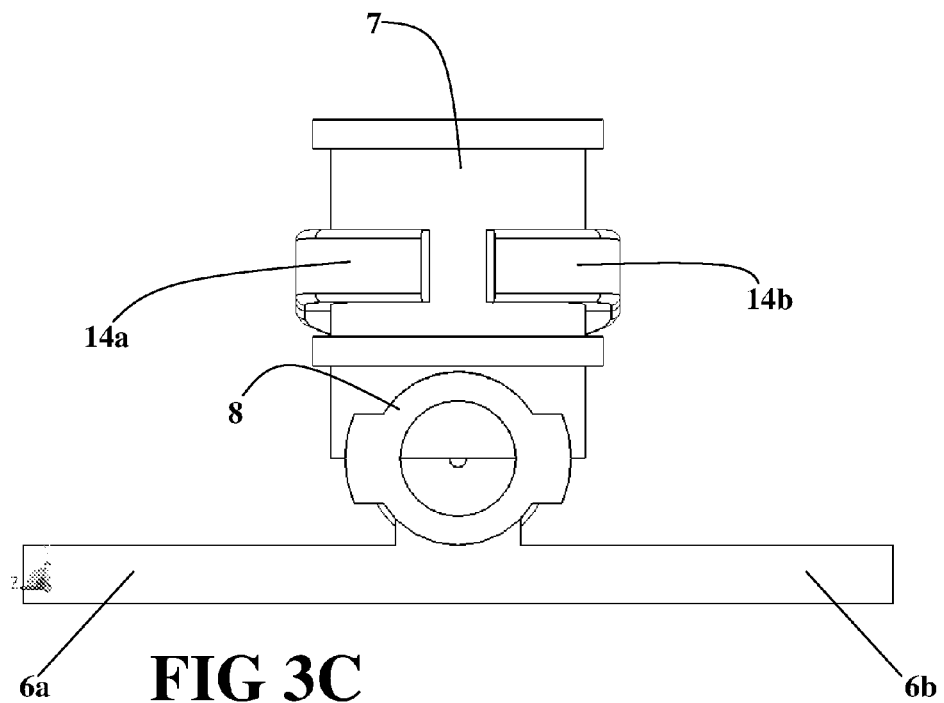
Figure 3D:
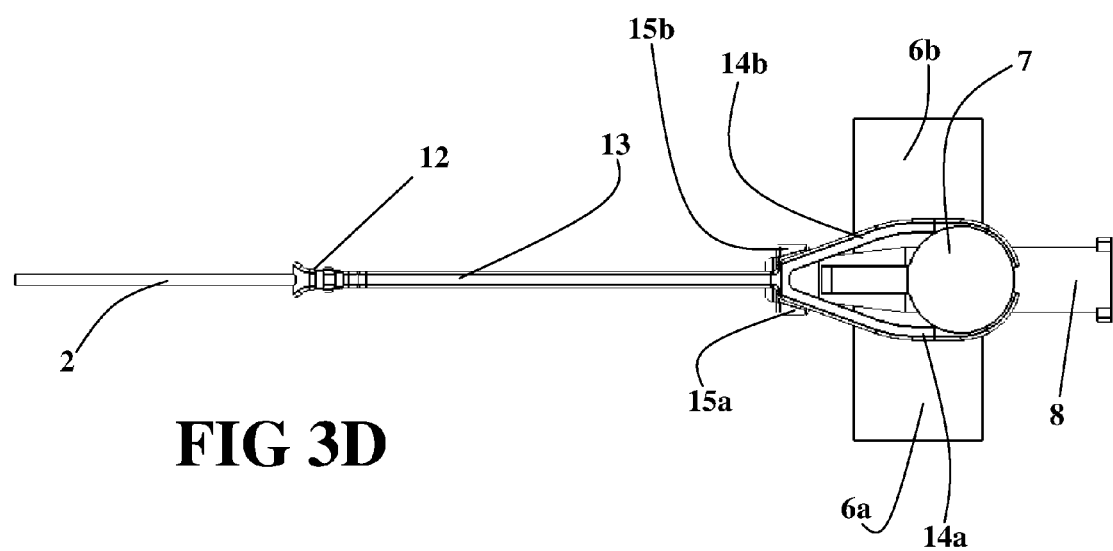
Figure 3E:
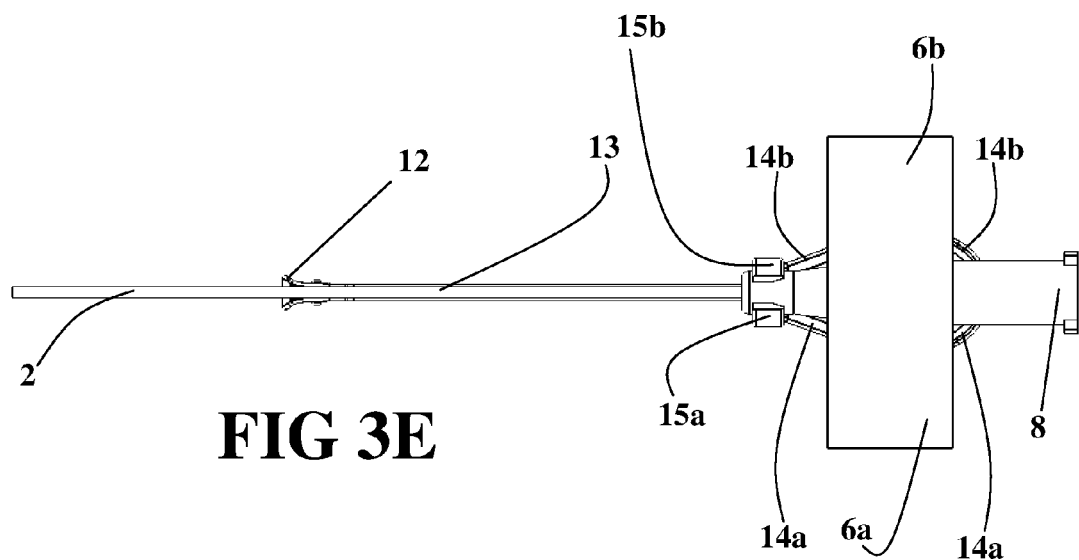

FIGS. 3A-3D show the forward arm 10 connected to IV catheter 1. It can be seen that the grasping arms 15a and 15b connect around hub 5 and arms 14a and 14b connect around valve 7. FIG. 3B shows a perspective side view of forward arm 10 connected to IV catheter 1, FIG. 3C shows a perspective back view of it, FIG. 3D shows a perspective top view of it and FIG. 3E shows a perspective bottom view of it.

Figure 4A:
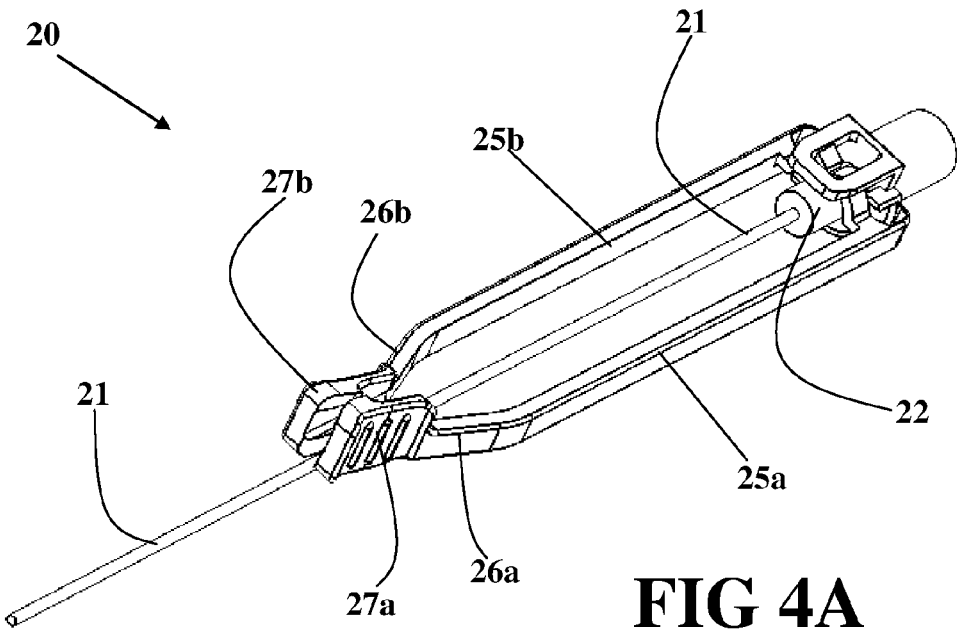
FIGS. 4A-4G illustrate perspective views of the needle holder of the present invention at different angles.
Figure 4B:
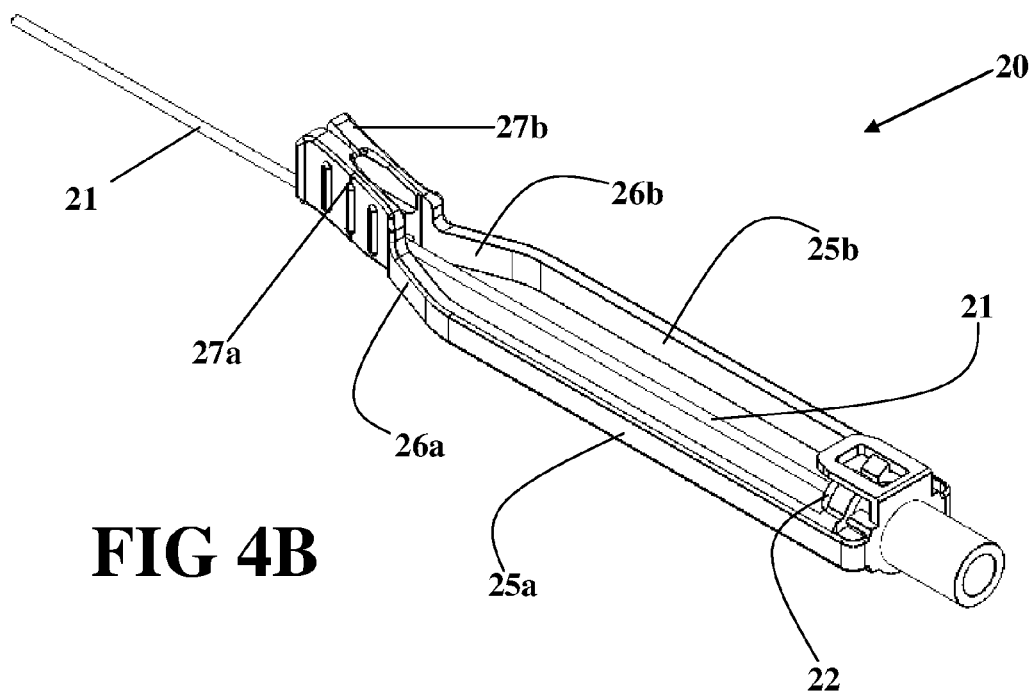
Figure 4C:
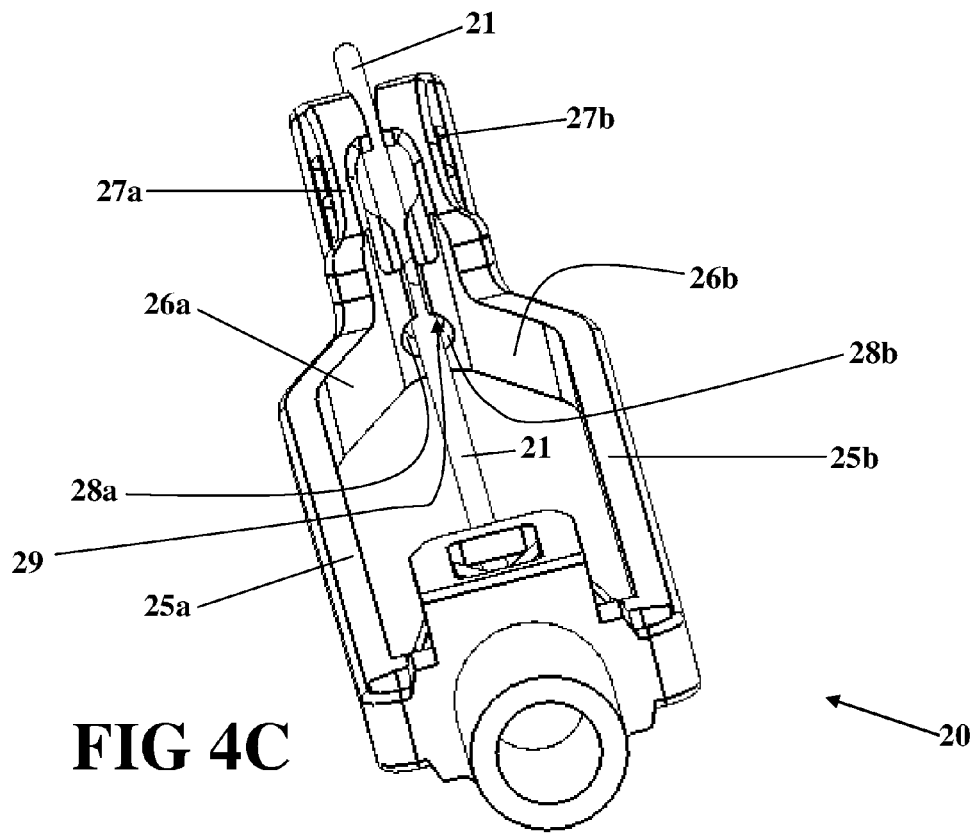

The present invention comprises a needle holder unit 20. The needle holder unit 20 comprises a puncturing needle 21 distally connected to a proximal hub 22, as shown in FIGS. 4A-4G. The needle holder unit 20 further comprises two side arms 25a and 25b connected to the proximal hub 22 at their proximal ends. The connection of arms 25a and 25b to the proximal hub 22 can be by snap connection, being glued thereto or by molding them thereto (or being constructed as one piece). The side arms length is usually between 3 cm and 8 cm, preferably 5 cm. Optionally, they are 3-5 cm shorter than the cannula 2 length. Its width is usually between 0.5 cm and 5 cm, preferably 1.0 cm. The two side arms 25a and 25b comprise slanted portions 26a and 26b at their distal ends closing in until being close to each other at their distal ends (i.e. such that the distal ends are disposed near to each other). The portions of the two side arms 25a and 25b proximal to slanted portions 26a and 26b are generally straight and parallel (and parallel to needle 21). At their distal ends, the slanted portions 26a and 26b are connected to forward finger grips 27a and 27b. The forward finger grips 27a and 27b act as protection plates to the cannula and enable finger grasping of them which actually holds the needle holder unit 20. The forward finger grips 27a and 27b are substantially parallel to each other (and to the needle) and comprise inner notch portions 28a and 28b with half circular inner portions (half tunnel portions) forming a hollow passage 29, wherein needle 21 passes therethrough, as shown in FIG. 4C. According to a preferred embodiment, the forward finger grips 27a and 27b also hold and/or secure middle section 13 therebetween.

Figure 4D:
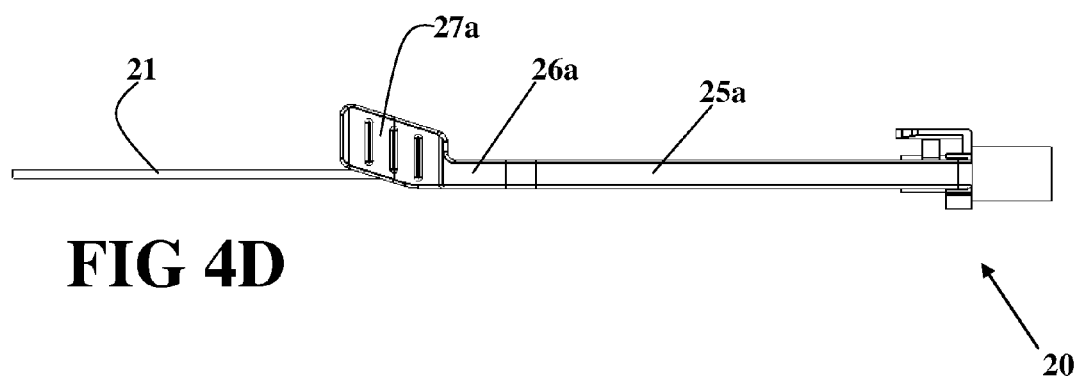
Figure 4E:
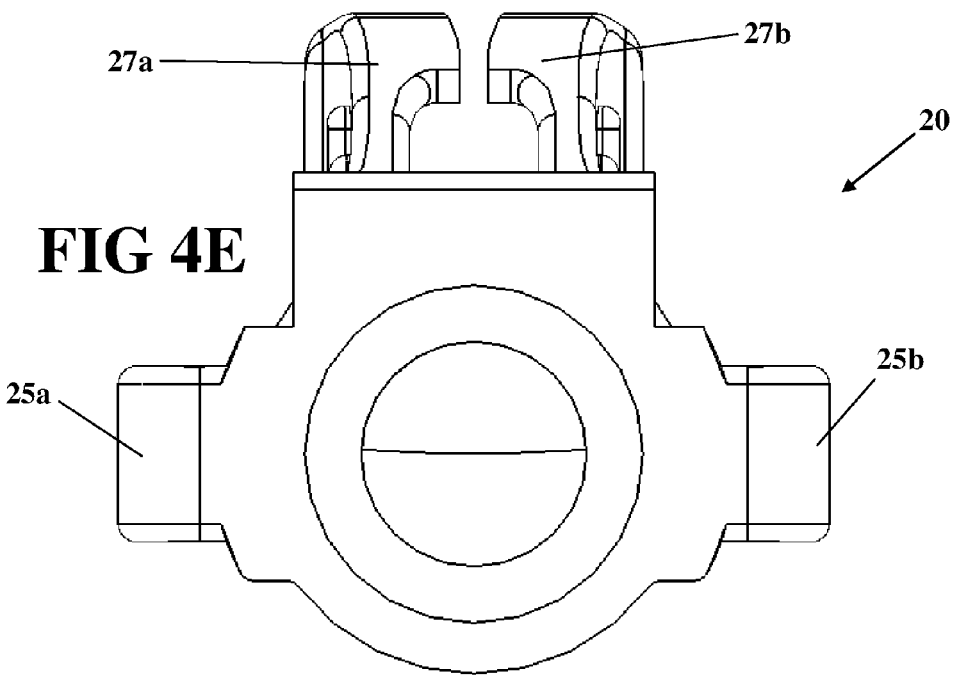
Figure 4F:
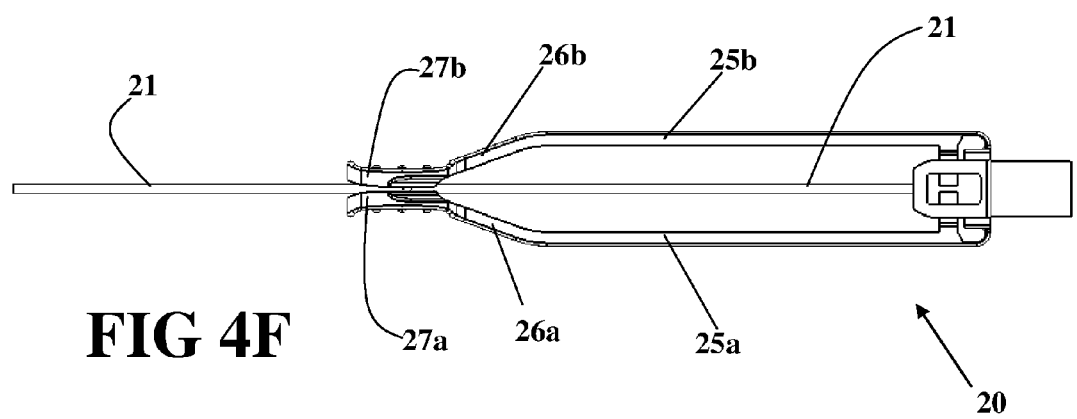
Figure 4G:
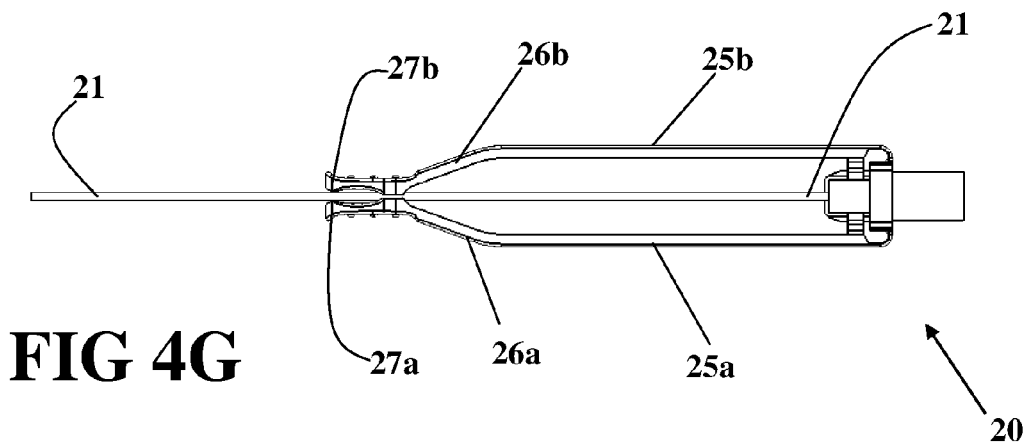

FIGS. 4A-4G show the needle holder unit 20. FIG. 4D shows a perspective side view of the needle holder unit 20, FIG. 4E shows a perspective back view of it, FIG. 4F shows a perspective top view of it and FIG. 4G shows a perspective bottom view of it.

During the initial state of use, needle holder unit 20 is connected to IV catheter 1. The needle 21 passes through hollow cannula 2 forming a united structure 30, as shown in FIGS. 5A-5F. A portion of hub 22 is configured to pass through and be fixed to the inner hollow portion of hollow end portion 8 (not shown). The needle 21 protrudes from hollow cannula 2. Middle section 13 of forward arm 10 (connected to catheter 1) and the two side arms 25a and 25b provide further protection of cannula 2, and generally prevent fingers from touching cannula 2 from the upper and side portions.

The needle holder unit is preferably made from any medical grade polymers, preferably Poly propylene or other flexible polymer.

The needle 21 length is usually between 5 cm and 15 cm and preferably 9 cm. Its diameter is usually between 0.25 mm and 1.2 mm and preferably 0.8 mm. It is preferably comprised of stainless steel.

The hub 22 length is usually between 1 cm and 4 cm and preferably 2 cm. Its diameter is usually between 0.5 cm and 1.5 cm and preferably 0.6 cm.

The arms 25a and 25b (including the slanted portions 26a and 26b) length is usually between 4 cm and 10 cm and preferably 6 cm. their width is usually between 1 mm and 5 mm and preferably 3 mm. their thickness is usually between 1 mm and 3 mm and preferably 2 mm.

The slanted portions 26a and 26b (alone) length is usually between 0.5 cm and 3 cm and preferably 1 cm. their width is usually between 1 mm and 5 mm and preferably 3 mm. their thickness is usually between 1 mm and 3 mm and preferably 2 mm.

The forward finger grips 27a and 27b length is usually between 3 mm and 20 mm and preferably 12 mm. Their height is usually between 3 mm and 15 mm. their thickness is usually between 1 mm and 5 mm and preferably 2 mm.

The united structure 30 is applied to a patient when medical personnel (nurse, doctor, etc.) hold the united structure 30 and inserts the needle 21 into the blood vessel. The united structure 30 is shown in FIGS. 5A-5F. The needle 21 at that time is fixed and does not move distally/proximally in relation to the other elements. The medical personnel holds united structure 30 (usually in his right hand) by gripping arms 25a, 25b or 26a and 26b. The medical personnel can grasp forward finger grips 27a and 27b with his finger to obtain a more stable controllable hold of united structure 30. When the needle 21 punctures the blood vessel and blood flows between the needle 21 and within hollow, transparent cannula 2 the medical personnel observes that the cannula 2 tip is in the required blood vessel.

At this point, prior art devices require that the medical personnel take his other hand (usually left) and grasp the catheter (for pushing the cannula) proximal to the united structure and maneuver and push forward the proximal hand distally. This is uncomfortable as the grip is in the same vicinity as the other hand grips the needle distally. This causes a movement in the hand (usually right) holding the united structure and can cause the medical personnel to lose control of the stable grip and to accidentally pull the tip out of the blood vessel, thus requiring starting from the beginning and creating a new puncture, etc. Furthermore, the left hand grasping the proximal pushing handle often touches proximal portions of the united structure when trying to grasp the proximal handle (e.g. when trying to find the proximal grip). This often causes moving the structure out of place and an accidental pull out from the blood vessel.

The present invention enables a comfortable insertion without the aforementioned prior art factors that cause accidental pullout. The forward handle 10 enables to quickly insert the cannula 2 in the blood vessel. The forward handle 10 is especially suitable to insert longer catheters with better control and without touching the indwelling parts. Once the cannula 2 is even partially inserted in the blood vessel, there is no more hazarded of an accidental pullout. The medical personnel does not need to retrieve his left hand anywhere near the proximal end of united structure 30, thus there is no hazard of losing control or stability of the grip. Surely the medical personnel do not touch or move the proximal end of united structure 30 thus preventing unwanted shocks and movements.

Once the needle 21 is punctured and blood flows up cannula 2 the medical personnel moves the distal forward grip 12 distally. The distal forward grip 12 is connected to forward handle 10, and forward handle 10 is connected tightly to the hub 5 (attached proximally to cannula 2) of the catheter 1 and moves the cannula 2 (and all of catheter 1) distally accordingly, as explained herein. The medical personnel can push the distal forward grip 12 distally with one of his right hand fingers, while the other right hand fingers grasp the gripping arms. The medical personnel can alternatively push/pull the distal forward grip 12 distally with his left hand. In any case the pullout hazards due to the engagement of the proximal end of the united structure (as in prior art) cease to exist. This is especially advantageous when using a long IV catheter. The forward arm also decreases the chances of the IV catheter being touched (and contaminated) during insertion.

Once the cannula 2 is inserted into the blood vessel as required, the needle holder unit 20 is proximally retrieved. The medical personnel holds the cannula 2 in place by gripping the distal forward grip 12. With his right hand he pulls the needle holder unit 20 proximally. When being moved proximally, and the slanted portions 26a and 26b reach the hub 5 (and/or grasping arms 15a and 15b and/or end portion 8 and/or other elements connected thereto) it causes the two side arms 25a and 25b to open sideways outwardly, thus a smooth retrieval and removal of needle holder unit 20 (with needle 21) is executed.

The needle holder unit 20 can be fully retrieved until the needle 21 totally exits hollow end portion 8, and thus needle holder unit 20 is removed and disposed of. The operation of the present invention has now been explained in connection with right handed personnel. For left handed personnel, the hands are usually reversed (whatever is comfortable).

After the needle holder unit 20 is removed the medical personnel removes and disposes of the forward arm 10. The forward arm 10 is disconnected from IV catheter 1 by disengaging (e.g. releasing the snap) the arms of downward grip 15 from hub 5, and lifting the proximal grip 14 from around valve 7. Then IV catheter 1 is fixed to the arm (or other body portion being punctured) by means of the wings, etc., as known in the art.

Figure 5A:
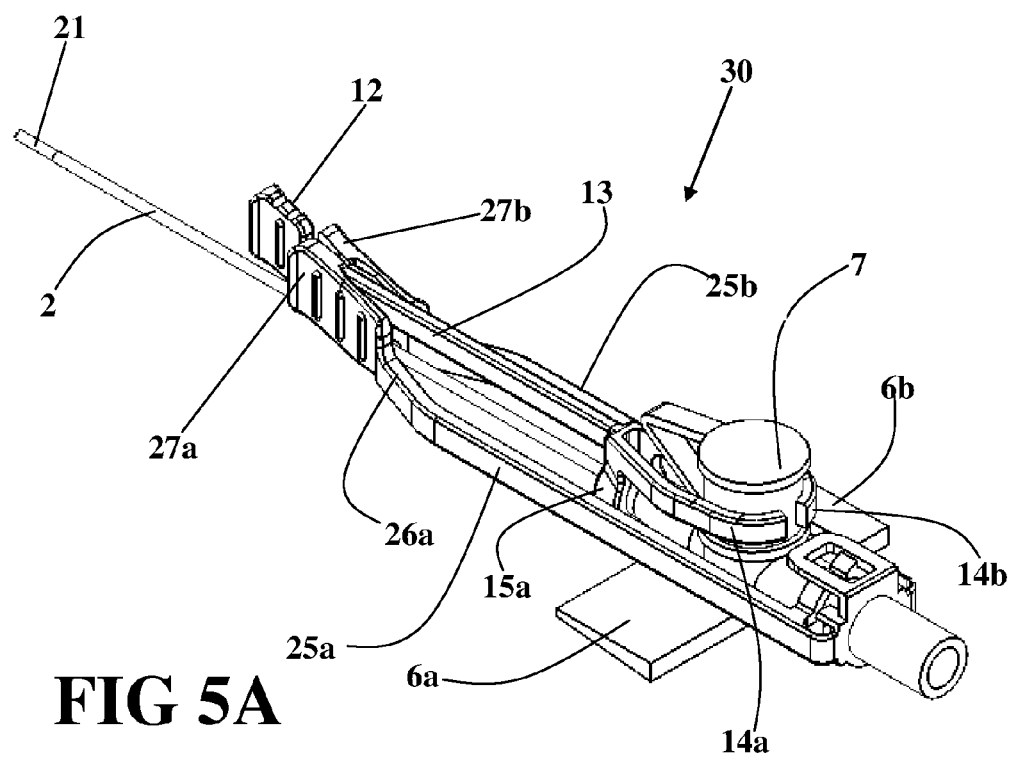
FIGS. 5A-5F illustrate perspective views of the united structure of the present invention at different angles.
Figure 5B:
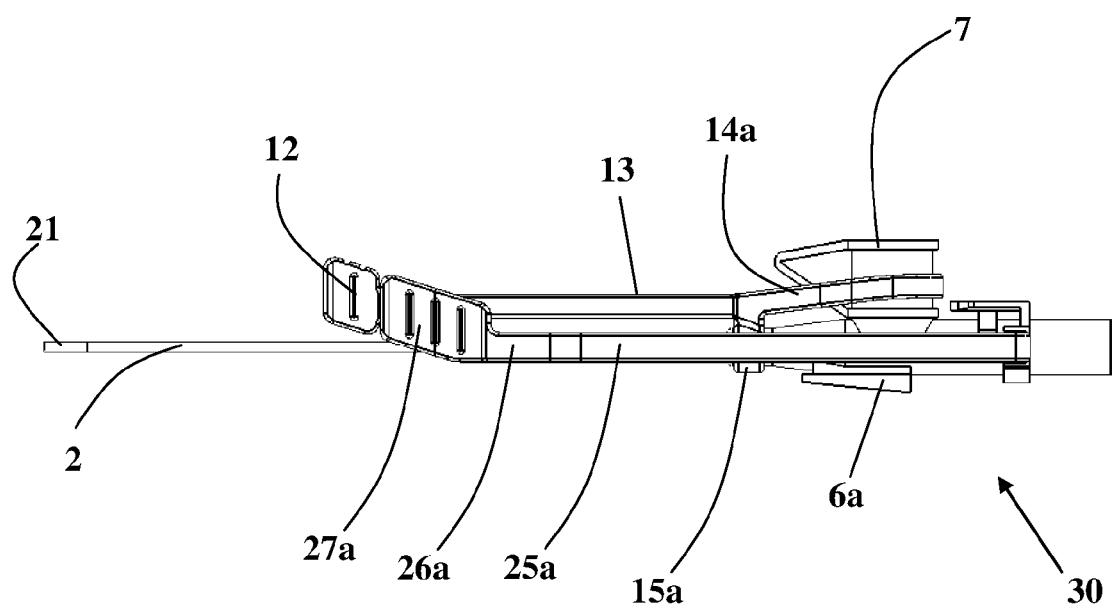
Figure 5C:
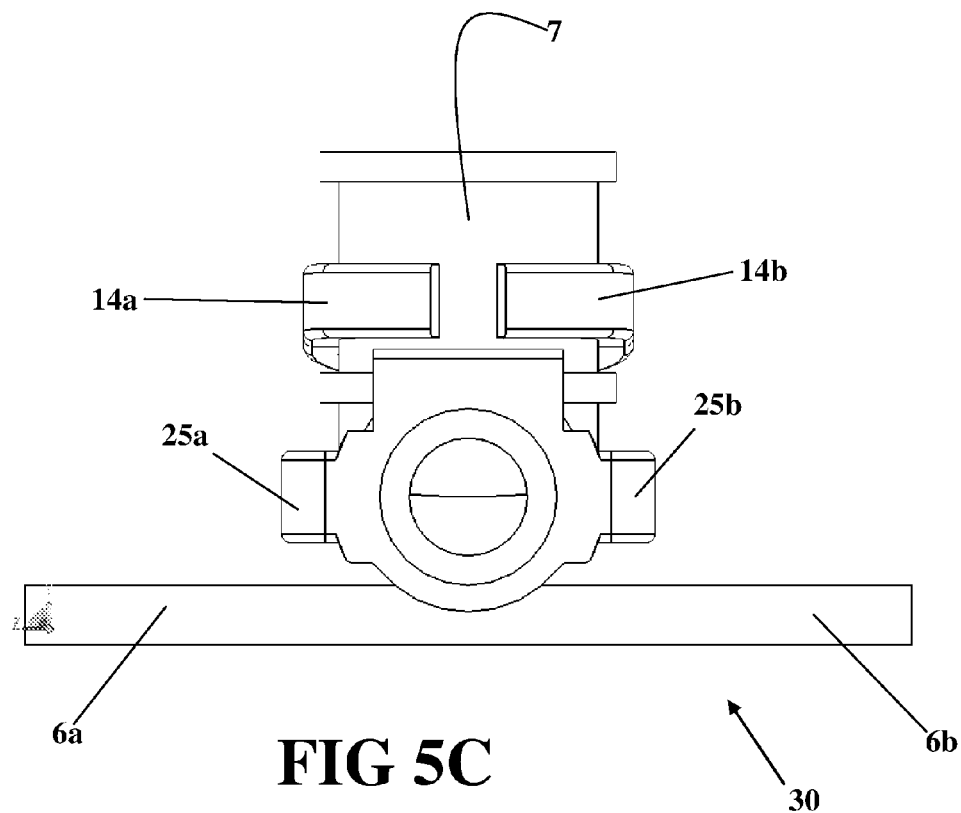
Figure 5D:
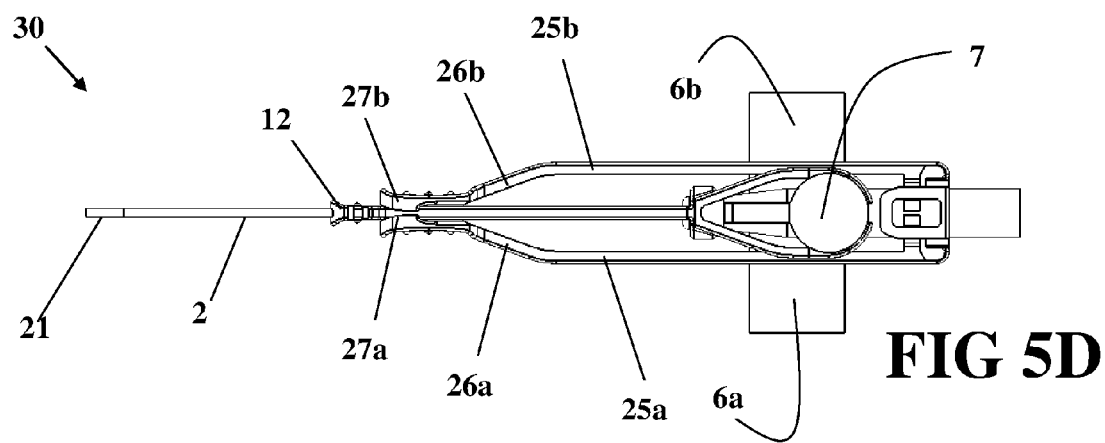
Figure 5E:
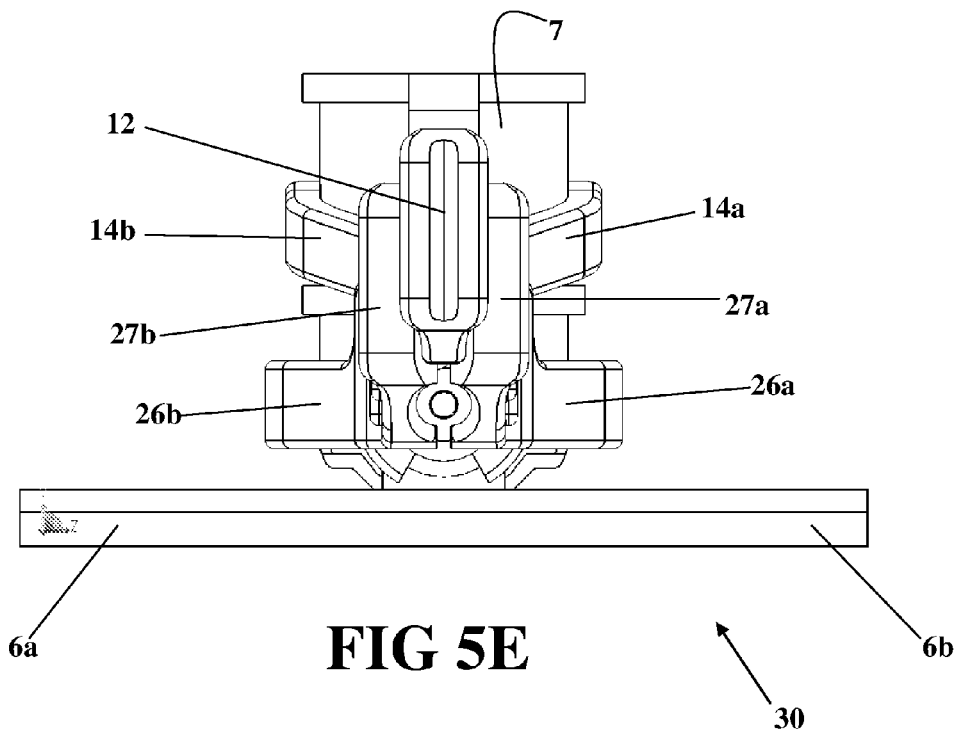
Figure 5F:
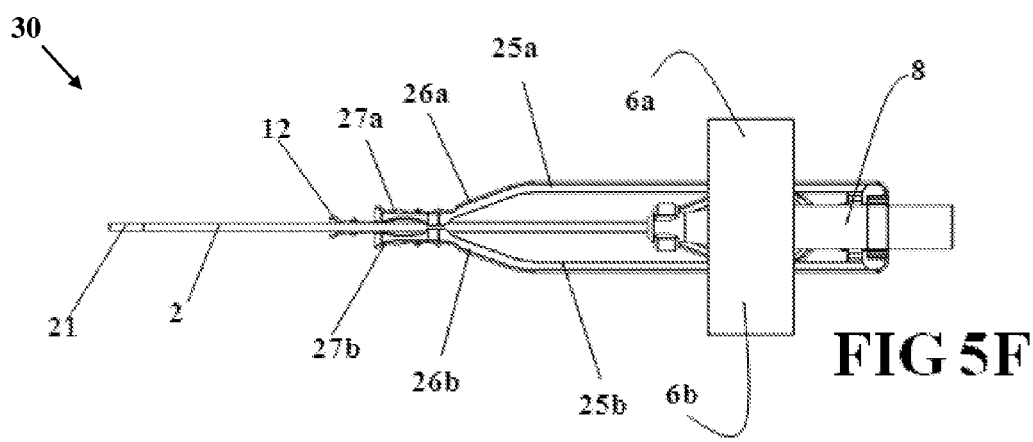

FIGS. 5A-5F show the united structure 30. FIG. 5B shows a perspective side view, FIG. 5C shows a perspective back view of it, FIG. 5D shows a perspective top view of it, FIG. 5E shows a perspective front view of it and FIG. 5F shows a perspective bottom view of it.

Figure 6A:
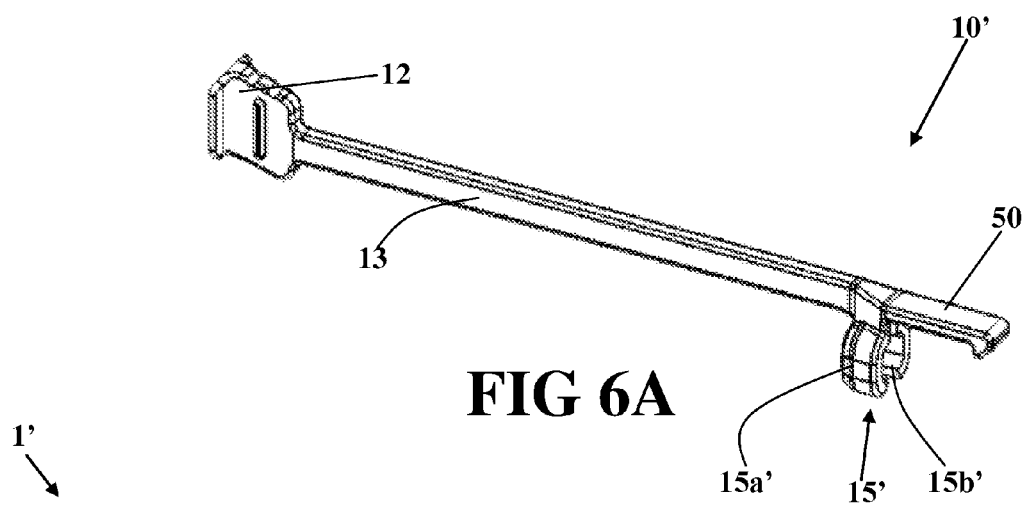
FIGS. 6A-6H illustrate perspective views of additional embodiments including another forward arm and a catheter closing unit.
Figure 6B:
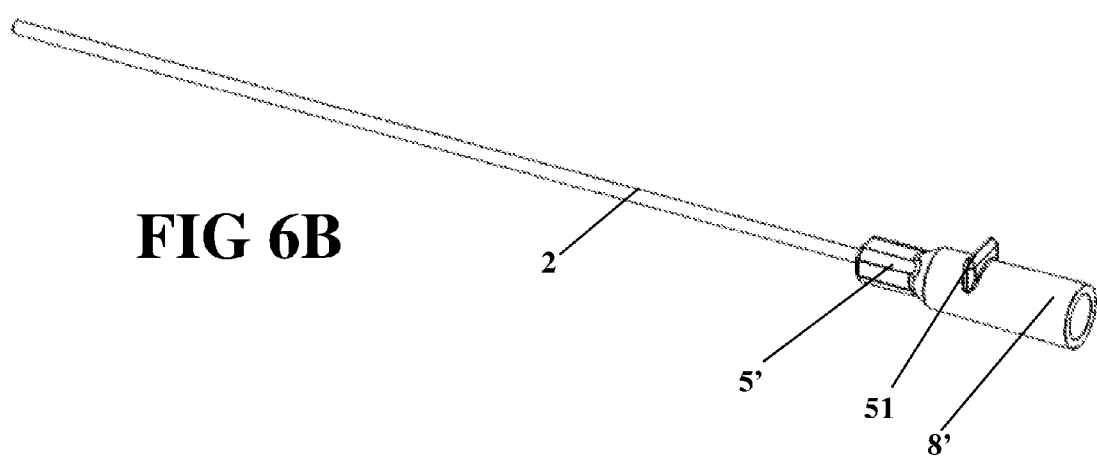
Figure 6C:
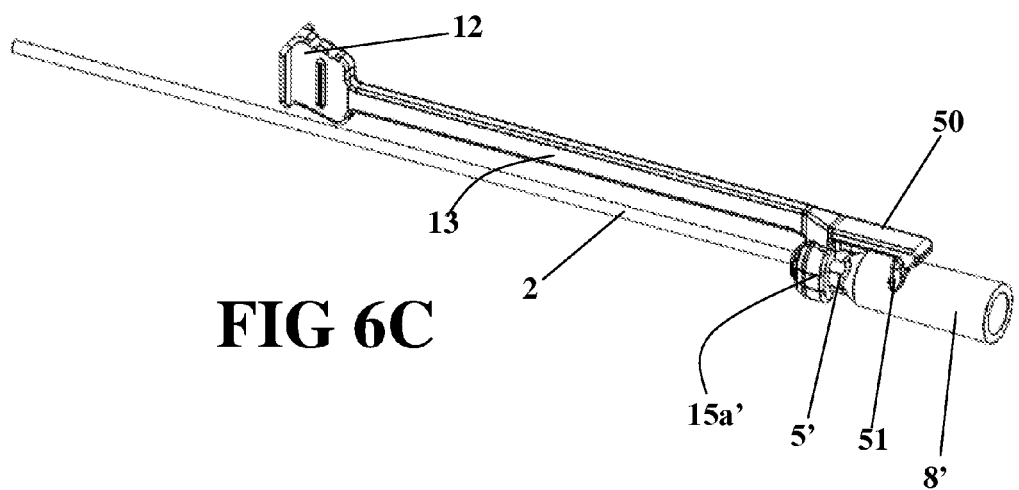
Figure 6D:
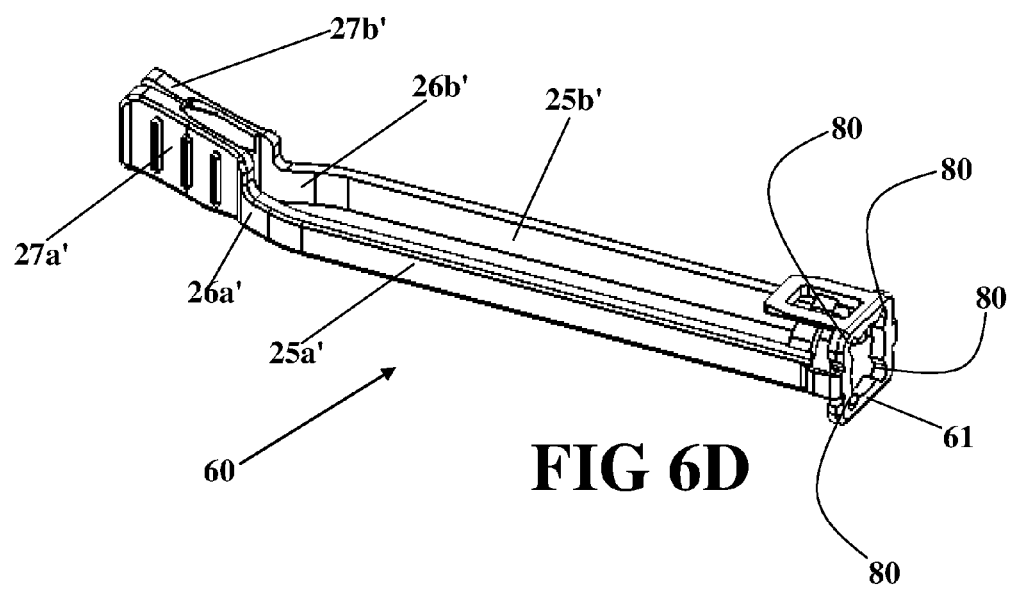
Figure 6E:
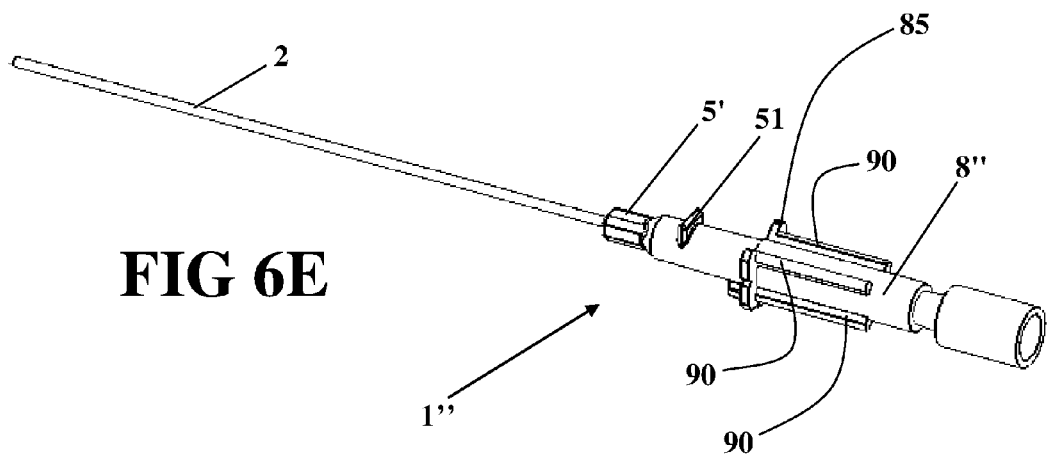
Figure 6F:
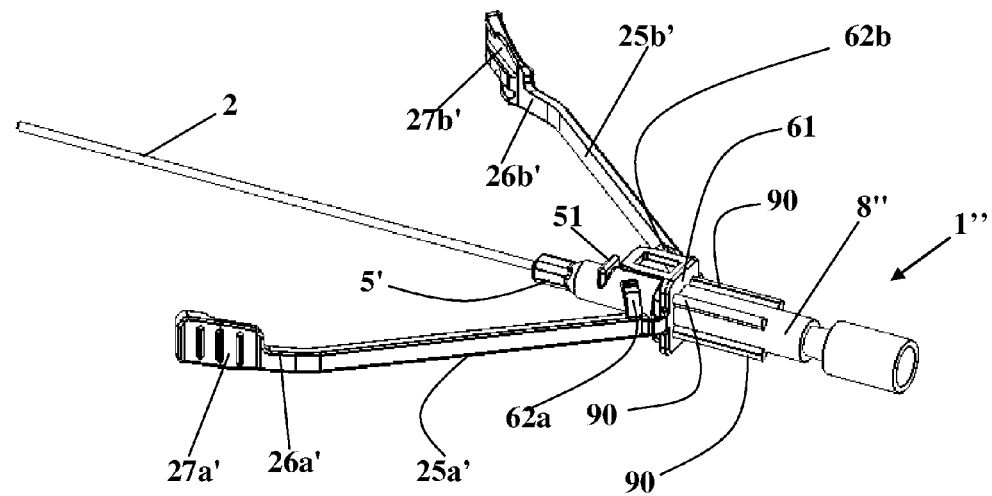

According to another embodiment, the forward arm and a needle unit are adapted to connect to any IV catheter. FIGS. 6A-6H show an embodiment wherein the present invention comprises a forward arm 10' (FIG. 6A) adapted to be connected to an existing IV catheter, e.g. IV catheter 1' (FIG. 6B). The forward arm 10' comprises a distal forward grip 12 for advancing the IV catheter 1' distally (the specific IV catheter 1' shown in FIG. 6B does not comprise wings).

The forward arm 10' comprises a proximal liftable gripper 50 adapted to grip and connect to a flat protrusion 51 on proximal hollow end portion 8' of IV catheter 1' (and on proximal hollow end portion 8" of IV catheter 1" in FIGS. 6E-6H). The proximal liftable gripper 50 comprises a proximal protrusion extending downwards with a distal flat portion adapted to grip and be placed at the proximal side of flat protrusion 51. The IV catheter 1' further comprises a hollow hub portion 5' connected proximally to the cannula 2. The forward arm 10' comprises a middle section 13 connecting between the distal forward grip 12 and the proximal gripper 50. The forward arm 10' further comprises a downward grip 15' comprising two grasping arms 15a' and 15b' adapted to connect around hub 5' (preferably a snap-on tube clip connection wherein downward grip 15' snaps on hub 5') of IV catheter 1'.

The forward arm 10' can be easily disconnected from IV catheter 1' after the insertion of the IV catheter 1' by releasing the gripper 50 from protrusion 51 (by lifting it upwards), and disengaging the arms of downward grip 15' from hub 5'.

The forward arm 10' size and materials are similar to those of forward arm 10 (the mutual portions thereof). The gripper 50 length is usually between 8 mm and 20 mm.

The protrusion 51 height is usually between 2 mm and 6 mm. Its thickness is usually between 1 mm and 2 mm.

According to another embodiment of the present invention, the present invention comprises a catheter closing unit 60 (FIG. 6D) comprising elements similar to that of the needle holder unit 20 (e.g. side arms), just without the needle and with proximal attachment means adapted to connect to an IV catheter e.g. IV catheter 1" (FIGS. 6E-6H). The catheter closing unit 60 functions in a similar manner as the needle holder unit 20 and provides protection to the cannula. The catheter closing unit 60 further comprises two side arms 25a' and 25b'.

According to one embodiment the catheter closing unit 60 attachment means comprises a proximal stabilizing grip 61 which comprises a hollow surface (preferably corresponding in shape and) adapted to be round about (close fitting around) the catheter hub (or proximal end portion) surface. The grip 61 hollow surface is slid distally round about the catheter hub (or proximal end portion) surface and retained by it.

In the example of FIGS. 6E-6H, the hollow surface is circular with four smaller circular portions 80 forming the corners of a square. The grip 61 hollow surface is adapted to be slid along catheter 1" proximal hollow end portion 8" comprising longitudinal cylindrical protrusions 90 along the proximal hollow end portion 8", parallel to each other and equally distanced from one to the adjacent other (corresponding in shape to the smaller circular square corner portions). Preferably, a stopper 85 is placed around the proximal hollow end portion 8" at a certain location for stopping the grip 61 when it is slid distally and is in the correct location for use. Preferably, the stop location is at the circumference at the distal end of the longitudinal cylindrical protrusions 90. The stopper 85 preferably comprises the shape of the hollow end portion 8" at the stop location.

The side arms 25a' and 25b' are attached to the proximal grip 61. The Connection of arms 25a' and 25b' to the proximal grip 61 can be by snap connection, being glued thereto or by molding them thereto (or being constructed as one piece). The sliding is executed while the two side arms 25a' and 25b' are in an open state. The side arms 25a' and 25b' comprise snaps 62a and 62b near their proximal ends. The snaps 62a and 62b extend inwardly from the inner sides of the side arms 25a' and 25b'. The snaps 62a and 62b each comprise two inwardly curved arms that are configured to snap on the hub or proximal hollow end portion 8" in a snap-on tube clip connection. When the grip 61 is fully slid, the side arms 25a' and 25b' are folded inwards towards the catheter and the snaps 62a and 62b snap on to the catheter hub (or proximal hollow end portion 8"), thus fixing the side arms 25a' and 25b' thereto.

The two side arms 25a' and 25b' comprise slanted portions 26a' and 26b' at their distal ends closing in until being close to each other at their distal ends (i.e. such that the distal ends are disposed near to each other). The portions of the two side arms 25a' and 25b' proximal to the slanted portions are generally straight parallel. At their distal ends, the slanted portions 26a' and 26b' are connected to forward finger grips 27a' and 27b'. The forward finger grips 27a' and 27b' comprise inner notch portions with half circular inner portions (half tunnel portions) forming a hollow passage (similar to hollow passage 29), wherein the IV catheter can pass therethrough. According to a preferred embodiment, the forward finger grips also hold and/or secure middle section 13 therebetween. Any appropriate needle can be used with the invention wherein it is passed through the IV catheter used.

After the IV catheter is inserted in to the blood vessel the catheter closing unit 60 and the needle used (not shown) are proximally pulled and disposed of in a similar manner as explained hereinabove regarding the needle holder unit 20. After the closing unit 60 and the needle used are removed the medical personnel removes and disposes of the forward arm 10'. The forward arm 10' is disconnected from IV catheter 1 by disengaging (e.g. releasing the snap) the arms of downward grip 15 from hub 5.

Figure 6G:
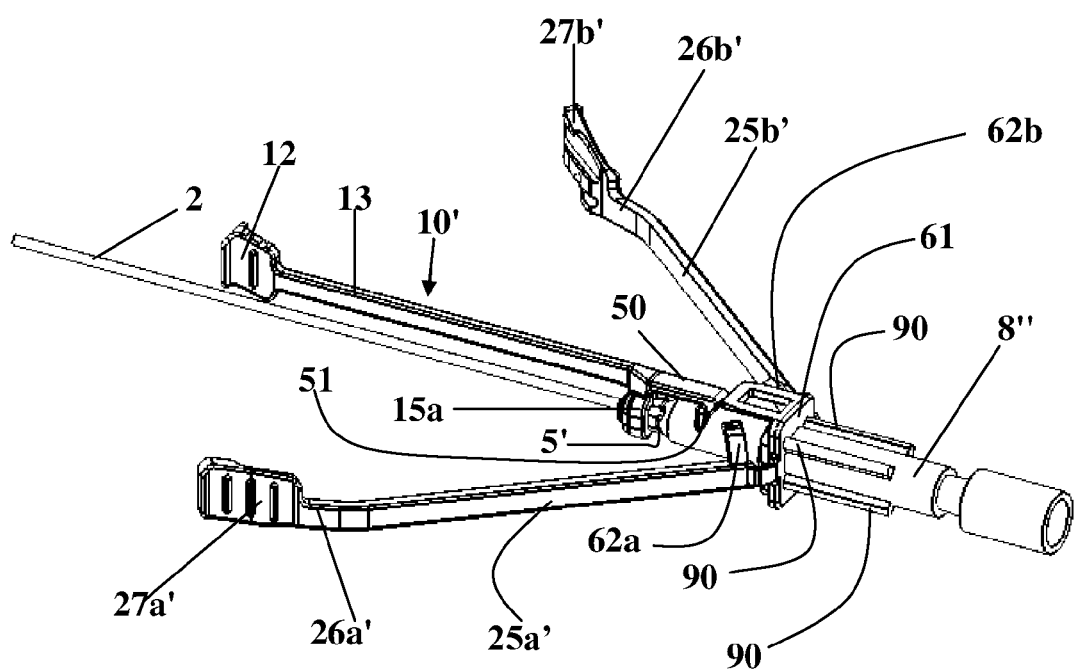
Figure 6H:
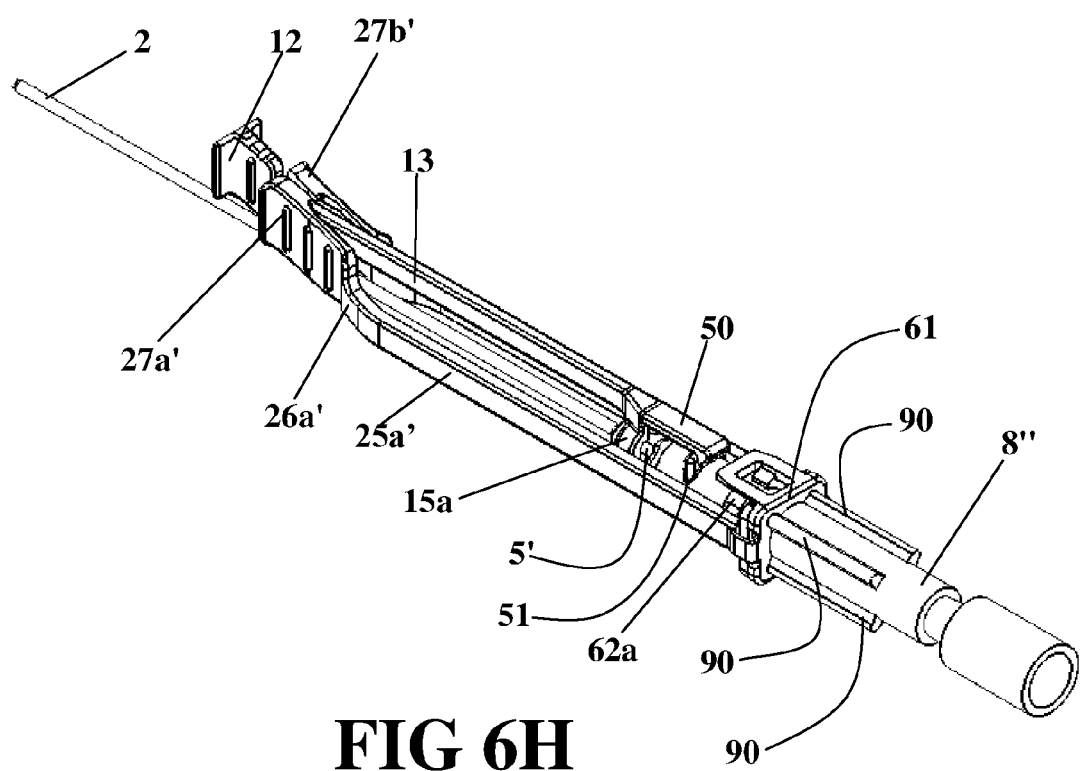

FIG. 6G shows both the forward arm 10' and the catheter closing unit 60 connected to the IV catheter 1". FIG. 6H shows both the forward arm 10' and the catheter closing unit 60 connected to the IV catheter 1" with the arms of the catheter closing unit 60 closed and ready for use.

The side arms and forward arm are preferably made of Poly propylene, poly carbonate, ABS, Nylon, or any other suitable material.

The sizes and materials of the arms 25a' and 25b', slanted portions 26a' and 26b', forward finger grips 27a' and 27b', are similar to those of arms 25a and 25b, slanted portions 26a and 26b, forward finger grips 27a and 27b of needle holder unit 20.

The proximal stabilizing grip 61 thickness is between 0.8 mm and 3 mm and preferably 2 mm. The stopper 85 thickness is between 0.8 mm and 3 mm and preferably 2 mm. the portions of the stabilizing elements 90 and corresponding elements 80 can vary in shape and size for efficient fixation. As said, the catheter hubs and proximal end portions size can vary in accordance with standard catheters wherein the elements that are attached thereto sizes, vary accordingly.

The sizes of the side arms can vary and are usually shorter than the needle unit, at the distal end, by 2 cm-6 cm.

Preferably, the forward arm is comprised of flexible material. This allows the pulling of the cannula in various angles (between the forward arm and the cannula). This assists in preventing the hand of the user clinician to be blocked by the patient's hand, and enables the user to pull at a higher angel.

According to a preferred embodiment of the present invention the forward arm 110 (FIGS. 7A-7D) comprises a middle section 113 comprising a distal portion 113a connected to the forward grip 12 and a thinner proximal portion 113b connected to the downward grip 115. The downward grip 115 comprises two grasping arms 115a and 115b adapted to connect around a catheter hub (preferably a snap-on tube clip connection as explained hereinabove).

The distal portion 113a is similar in size (width and thickness) and material as the forward arm middle section explained herein. The proximal portion 113b is preferably thinner than distal portion 113a and is flexible. The proximal portion can have different cross section geometry than distal portion 113a to enable for a differential in flexibility. The proximal portion 113b comprises flexible material, and is preferably made of a material selected from the group consisting of poly propylene, poly ethylene or nylon.

The proximal portion 113b length is usually between ¼ to ¾, from the total length of the forward arm and preferably a ⅓ of it (wherein the total length of the forward arm 110 is similar to that of 10, 10'). Its width is usually between 1 and 4 mm, and preferably 2 mm. Its thickness is usually between 0.5 and 3 mm, and preferably 2 mm.

Using the forward arm 110 for inserting the IV catheter is similar to as explained hereinabove (with respect to forward arm 10 and 10') with the following difference/advantage. At the first stage the medical personnel user performs the puncture and pushes/pulls the forward arm 110 distally, parallel to the cannula 2. Once the cannula 2 is deep enough such that it could not accidentally pull out, the distal portion 113a (or forward grip 12) can be lifted upwards and thus the flexible proximal portion 113b bends. The medical personnel then can use his hand to fully insert the cannula 2 by simultaneously lifting distal portion 113a (or forward grip 12) and pushing/pulling distal portion 113a distally.

A typical scenario includes lifting the bottom portion of forward grip 12 with one finger (e.g. index finger) and pushing distal portion 113a distally with another finger (e.g. thumb). The distal portion 113a lifted can be at various angles in relation to the cannula 2. The angle can change simultaneously to the distal movement of the cannula 2. For example, the distal insertion begins at 0° and is fully inserted at 90°. Optionally the angle can reach 90° at half way (or before or after) and remain so until the full insertion. After the full insertion, the forward arm 110 is disconnected (e.g. by de-snapping downward grip 115).

This embodiment is advantageous in that that it enables (for example) insertion of a cannula in the forearm while the arm is folded. Insertion is done such that the puncture and insertion site is at the forearm. When the cannula is inserted distally and the distal part of the forward grip reaches the brachium, the distal portion 113a (or forward grip 12) is lifted upwards and the insertion is completed (as explained regarding this embodiment) with the arm still folded.

Figure 7A:
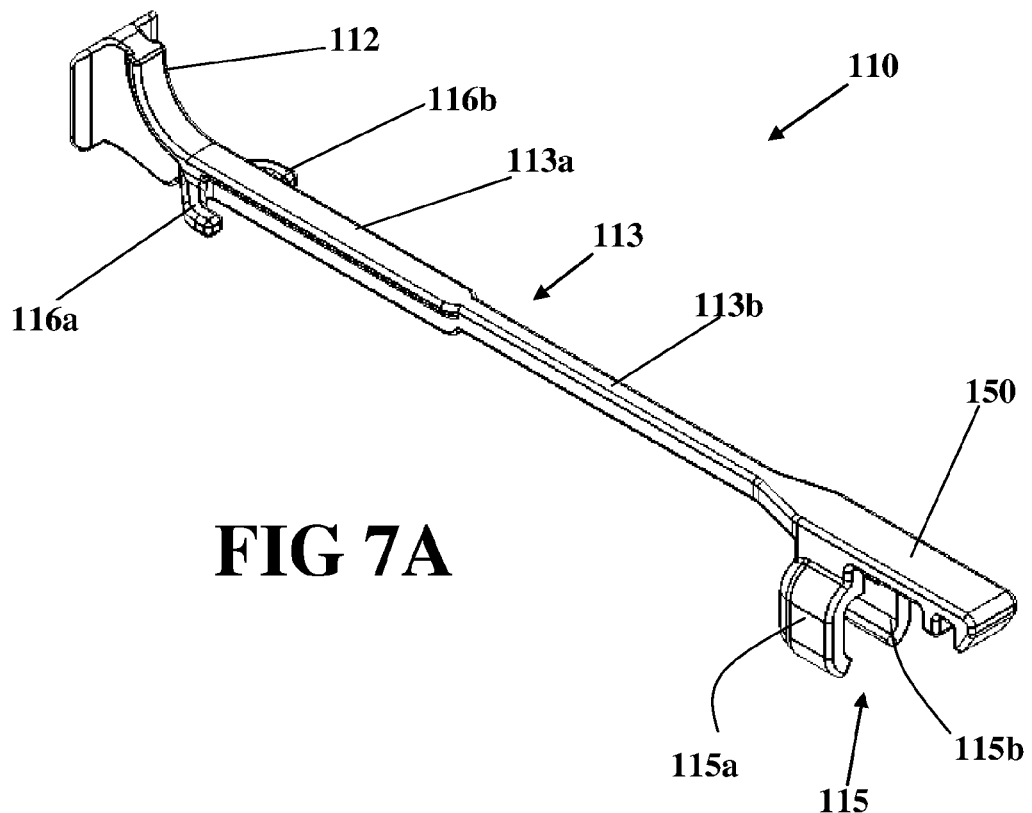
FIGS. 7A-7D illustrate perspective views of another embodiment of the forward arm.
Figure 7B:
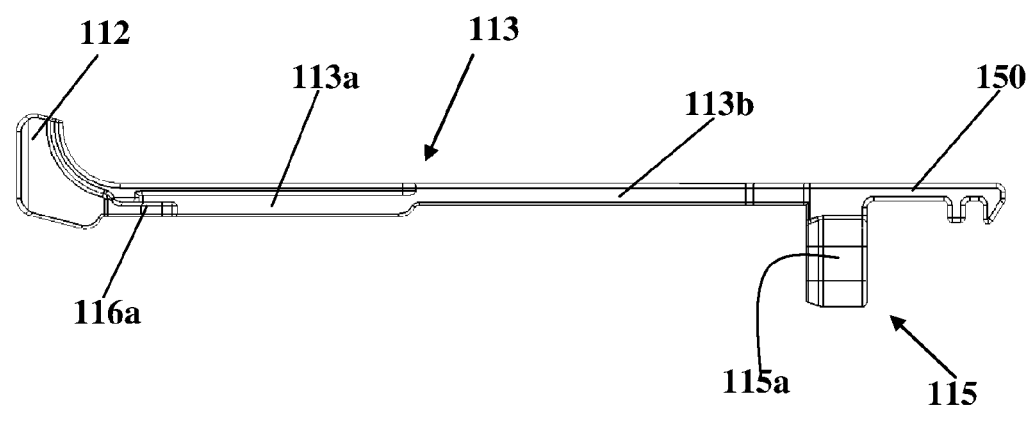
Figure 7C:
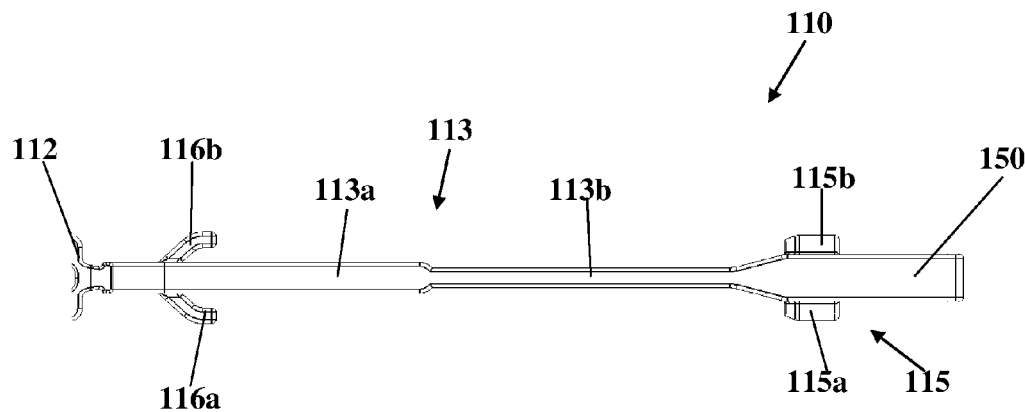
Figure 7D:
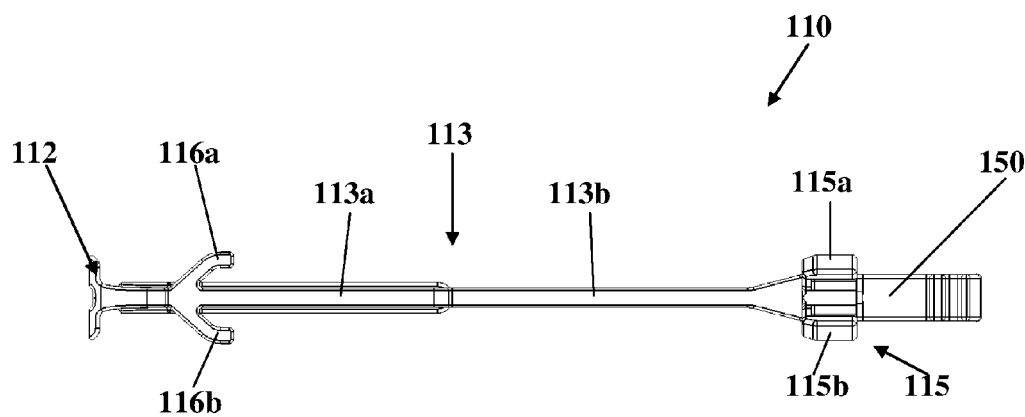

FIG. 7B shows a perspective side view of forward arm 110, FIG. 7C shows a perspective top view of it and FIG. 7D shows a perspective bottom view of it.

According to another embodiment of the present invention, the forward arm comprises two curved flaps 116a and 116b that extend outwardly and proximally from the distal end of middle section 113. The flaps 116a and 116b are configured to close and hold together forward finger grips 27a' and 27b' of catheter closing unit 60 (and similarly forward finger grips 27a and 27b of needle holder unit 20). This embodiment is advantageous in that it prevents the united structure 30 (catheter 1 with forward handle 110 and needle unit 20 (or catheter closing unit 60)) from breaking apart and keeps it in the pre-use stage and ready for use.

It should be noted that the embodiment with flexible proximal portion 113b can be along with the flaps embodiment or without it and vice versa. Both embodiments were drawn in FIGS. 7A-7D for convenience.

FIGS. 8A-8E show the forward arm 110, the catheter closing unit 60 and the IV catheter 1" put together and ready for use in insertion. The forward arm 110 with the curved flaps 116a and 116b hold at least the distal portions of forward finger grips 27a' and 27b' together. When medical personnel insert the cannula 2 into the body, the forward arm is moved distally and thus the flaps 116a and 116b move distally from the forward finger grips 27a' and 27b', thus unloosening them and enabling them to move sideways.

Figure 8A:
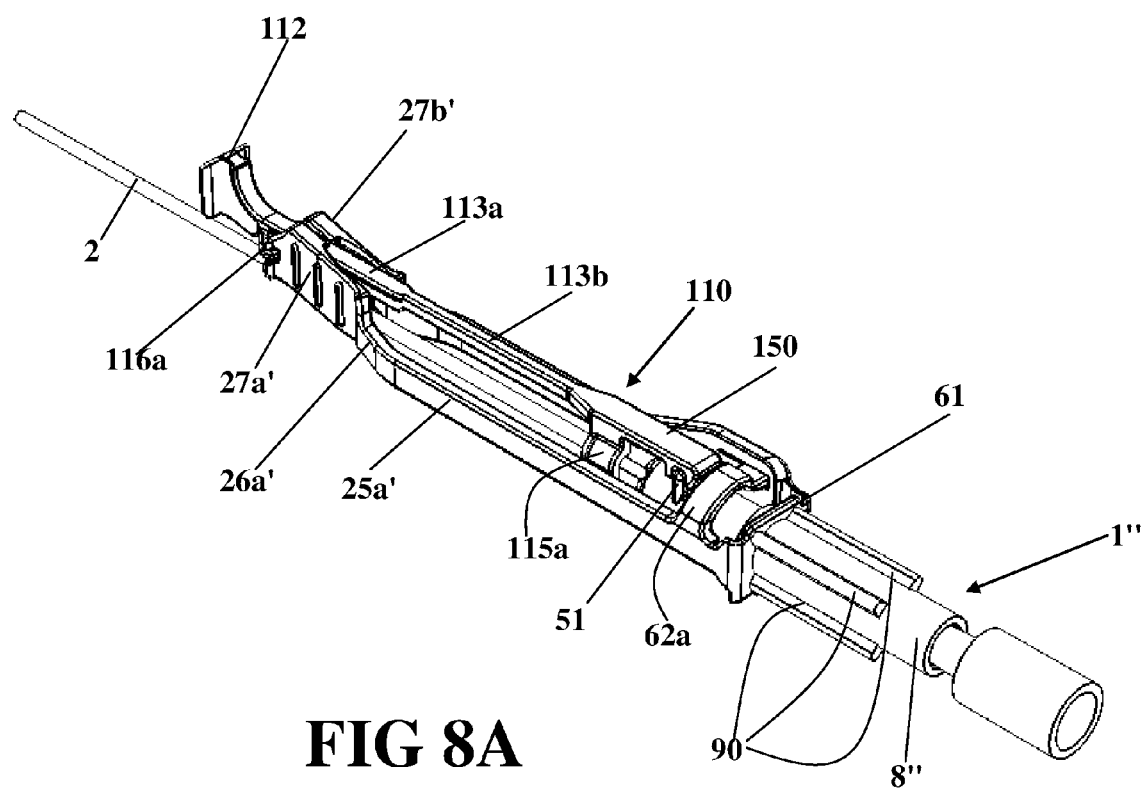
FIGS. 8A-8G illustrate perspective views of an embodiment relating to flaps and notches.
Figure 8B:
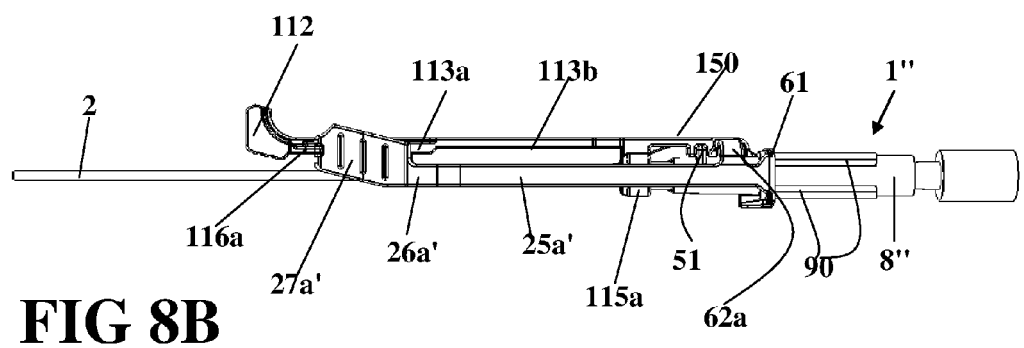
Figure 8C:
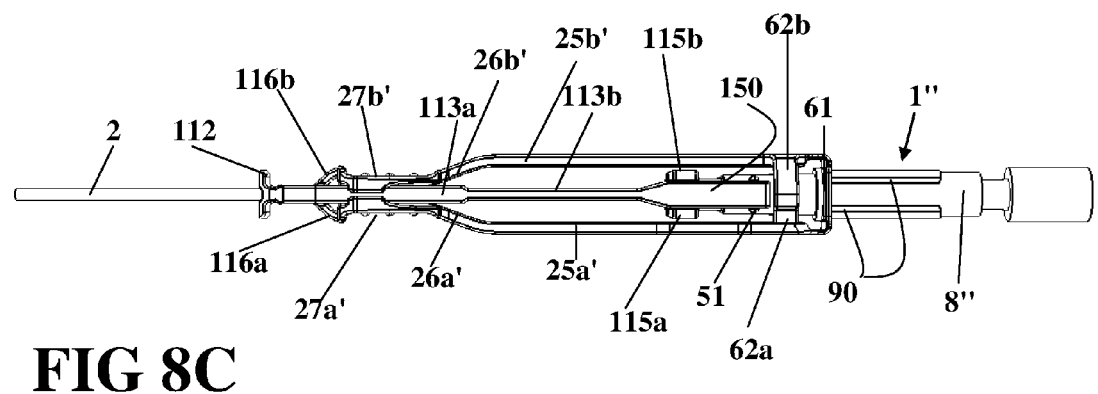
Figure 8D:
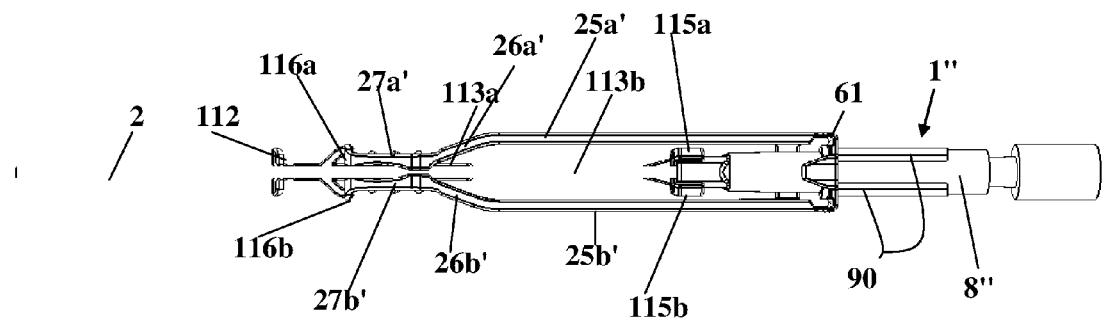

FIG. 8B shows a perspective side view of forward arm 110, the catheter closing unit 60 and the IV catheter 1" put together. FIG. 7C shows a perspective top view of them and FIG. 7D shows a perspective bottom view of them.

According to a preferred embodiment, the distal edges of the forward finger grips 27a' and 27b' each comprise a notch 117 on their distal outer side. The notches 117 are configured to receive the flaps 116a and 116b.

According to one embodiment, the forward finger grips 27a' and 27b' comprise a substantially flat outward protruding portion 118 at their distal surface edges with the notches 117 placed within these flat outward protruding portions 118.

Figure 8E:
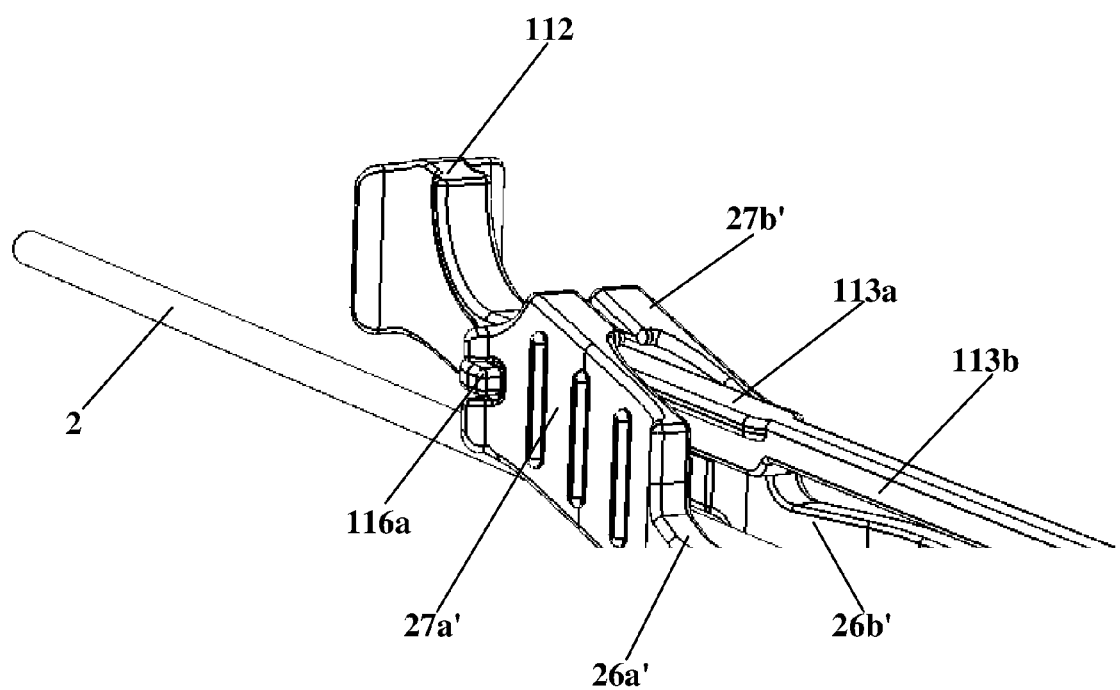
Figure 8F:
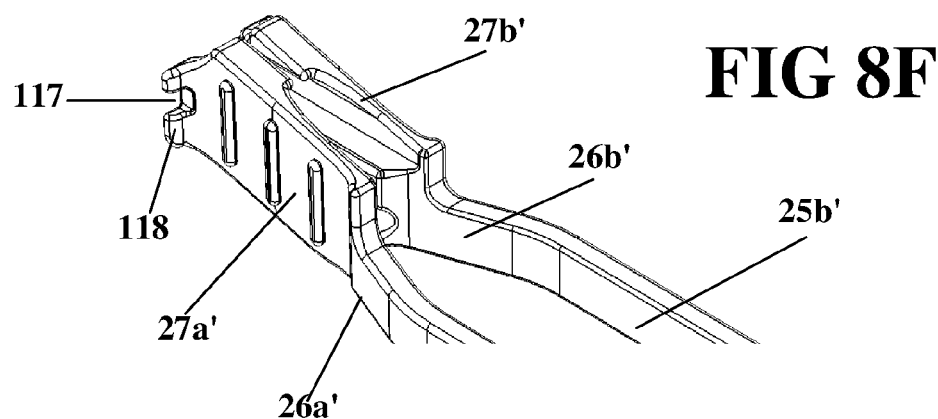
Figure 8G:
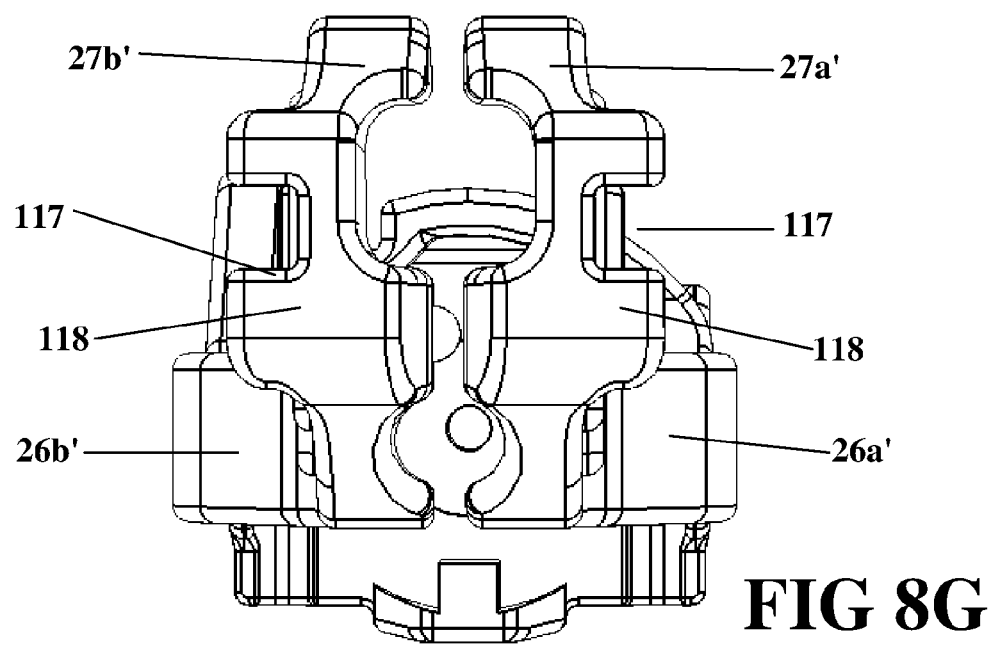

FIG. 8E shows the flaps 116a and 116b within the notches 117. FIG. 8F shows the forward finger grips 27a' and 27b' without the forward arm 110 and catheter 1" portions. FIG. 8G is a front view of the catheter closing unit 60 with the forward finger grips 27a and 27b (without the forward arm 110 and catheter 1") comprising the flat outward protruding portions 118 and the notches 117.

It should be noted that present invention also relates to the embodiments of the needle holder unit 20 in a similar manner to the aforementioned embodiments of the catheter closing unit 60 explained herein (and vice versa mutatis mutandis). For example, the structure, sizes and materials of the side arms, slanted portions, forward finger grips (and the notches), hollow passage, snaps (62a and 62b) as explained herein in regards to the catheter closing unit 60, are the same regarding these elements of an embodiment of the needle holder unit 20. Accordingly, according to one embodiment of the present invention, the forward arm 110' as explained herein is used with the corresponding embodiment of needle holder unit 20.

The flat outward protruding portions 118 length is usually between 4 mm and 15 mm and preferably 9 mm. Its width is usually between 1 mm and 8 mm and preferably 3 mm. Its thickness is usually between 1 mm and 4 mm and preferably 2 mm.

The flaps 116a and 116b length is usually between 2 mm and 15 mm and preferably 7 mm. their width is usually between 1 mm and 5 mm and preferably 3 mm. their thickness is usually between 1 mm and 5 mm and preferably 2 mm.

The notches 117 sizes are such that they are configured to receive the flaps 116a and 116b.

According to another embodiment of the present invention a safety needle mechanism is used. Safety vascular access needles are designed to obtain access to the vasculature of the patient along with providing protection to the medical personnel making it safe for him, such that the needle tip is protected thus preventing accidental needlestick to the medical personnel.

Figure 9A:
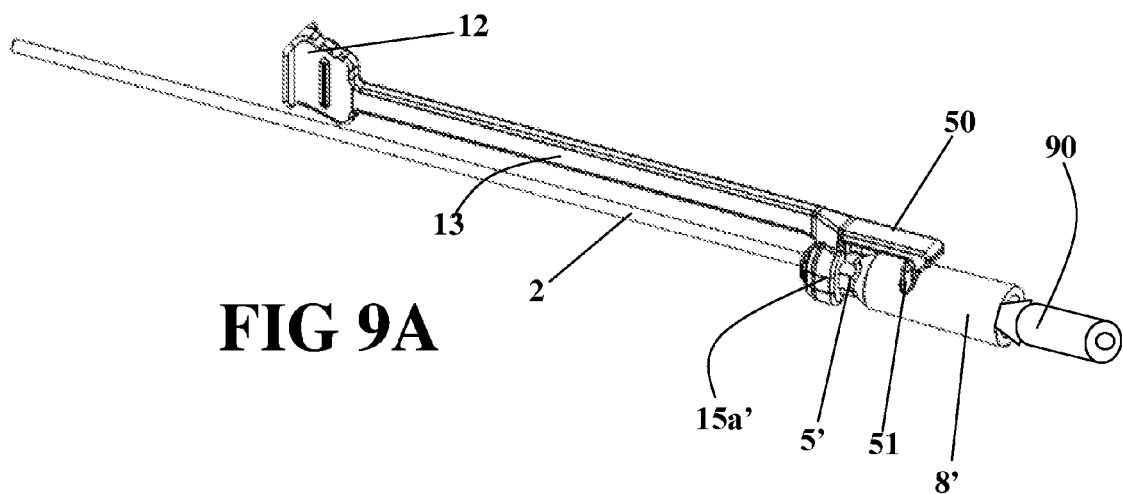
FIGS. 9A-9B illustrate perspective views of an embodiment relating to the safety capsule.
Figure 9B:
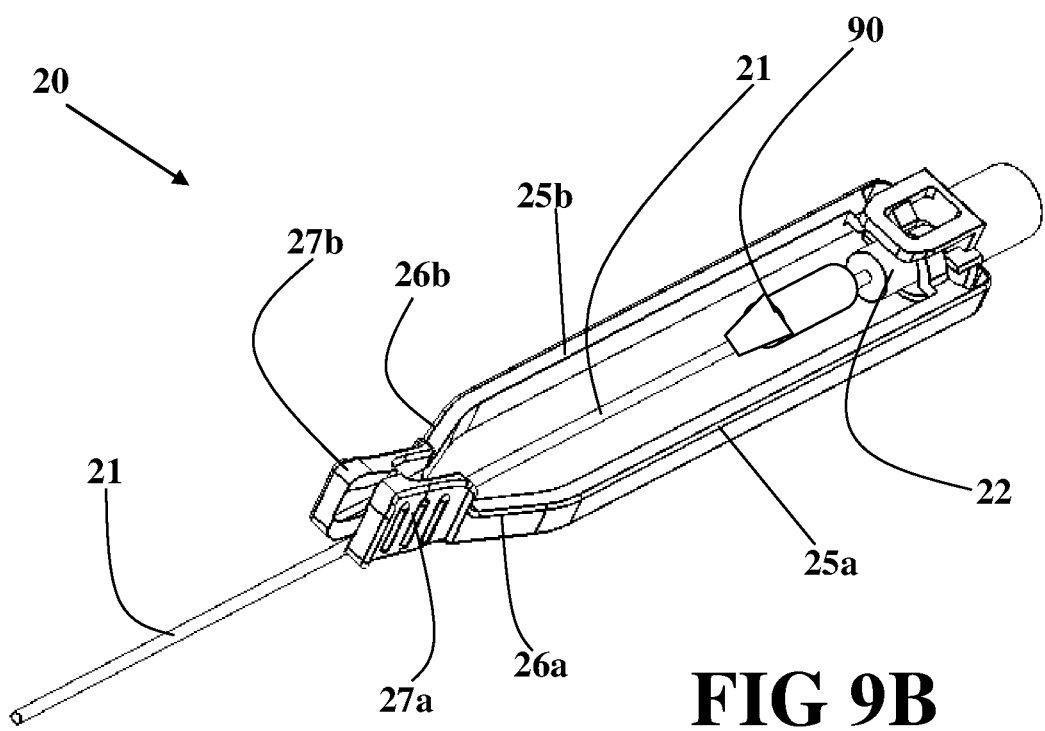

FIGS. 9A-9B illustrate an embodiment of the present invention comprising a safety capsule 90 (sometimes referred to as safety slider). The safety capsule 90 is a hollow preferably cylindrical tubular element which allows passage of needle 21 therethrough. The needle 21 is freely slidable in relation to safety capsule 90 (and the safety capsule 90 is slidable along needle 21). The safety capsule 90 automatically senses the end of the needle 21 and instantly locks out to fully encapsulate the distal needle tip of needle 21.

The safety capsule 90 is connected to the proximal side of the proximal hollow end portion (8, 8', 8") of IV catheter (1, 1', 1"), in a luer connection. Therefore, when the forward arm (10, 10', 110) is pushed/pulled distally (the handle is connected to the hub 5, 5') the safety capsule 90 moves distally accordingly along with end portion (8, 8', 8") (which is connected to hub 5, 5'). This safety feature eliminates the risk of getting accidently stuck with an introducer needle.

FIG. 9A shows the safety capsule 90 proximally attached to the proximal hollow end portion 8' in a luer connection. FIG. 9B shows the safety capsule 90 mounted on needle 21 of needle holder unit 20. Before insertion, safety capsule 90 is proximally attached to the proximal hollow end portion 8' of the catheter 1'. When needle 21 is fully inserted into the catheter 1' (and capsule 90 is proximally attached to the proximal hollow end portion 8'), the proximal portion of capsule 90 is thus in contact with the distal portion of hub 22.

According to one embodiment (not shown) the downward grip 15 is not connected to the hub (5, 5') but to the safety capsule 90 thus fixing forward arm (10, 10', 110) to the duckbill valve 95. The grasping arms 15a and 15b are adapted to connect around the safety capsule 90, preferably a snap-on tube clip connection wherein downward grip 15 snaps on safety capsule 90. Thus the catheter (1, 1', 1") moves distally/proximally in accordance with the forward arm (10, 10', 110) due to the fact that the cannula 2 is connected to the hub (5, 5') which is attached to proximal hollow end portion (8, 8', 8") which is connected (via luer connection) to safety capsule 90.

The length of safety capsule 90 is usually between 3 and 20 mm, and preferably 6 mm. Its diameter is usually between 3 mm and 15 mm, and preferably 8 mm. The capsule 90 preferably comprises one or more of the following materials: steel, titanium, polymer and a combination thereof. A commercial example of such capsule 90 is Certofix safety—by B. Braun. Another commercial example is Merit advance safety needle (by Merit Medical Systems Inc.). Another commercial example is Safety Vascular Access Needles (by ISIPS).

A puncturing needle with such safety capsule can be used with the catheter closing unit 60 and the IV catheter 1" and forward arm 110, put all together.

An example of the mechanism of the safety needle is such that the needle passes through a self-closing straight tweezers element. A portion of the needle a few millimeters before its point edge comprises a thicker portion such that when pulled proximally the thicker portion cannot pass through the proximal portion of the tweezers element. The thick portion is placed such that when it reaches the proximal portion of the tweezers element the distal edges of the distal closing arms of tweezers element close on the tip edge of the needle and the whole tweezers element sits on the distal portion of the needle, thus preventing accidental needlestick.

According to an embodiment of the present invention the safety mechanism sits within the end portion (8, 8', 8") of the catheter. According to an embodiment of the present invention the safety capsule 90 is configured such that it sits within the end portion (8, 8', 8").

According to another embodiment of the present invention, the present invention comprises a one-way valve connected in a luer connection to the proximal end of the hollow end portion (8, 8', 8") of catheter (1, 1', 1"). An example of such on-way valve is duckbill valve. The distal portion of the duckbill valve comprises synthetic elastomer, and is generally shaped like the beak of a duck, to prevent contamination due to backflow. The proximal end of the duckbill valve is configured to receive the puncturing needle. The duckbill valve distal end retains its natural flattened shape. When the needle (e.g. needle 21) is inserted distally, the distal flattened end partially opens to permit the needle to pass. When the needle is proximally removed, however, the duckbill distal end is in its flattened shape, preventing backflow of blood or other debris.

The duckbill valve is preferably placed in duckbill valve casing 95. The duckbill valve casing 95 is connected to the proximal side of the proximal hollow end portion (8, 8', 8") of IV catheter (1, 1', 1"), in a luer connection. Therefore, when the forward arm (10, 10', 110) is pushed/pulled distally (the handle is connected to the hub 5, 5') the duckbill valve casing 95 moves distally accordingly along with end portion (8, 8', 8") (which is connected to hub 5, 5').

FIG. 10 shows the duckbill valve casing 95 proximally attached to the proximal hollow end portion 8' in a luer connection. Before insertion, duckbill valve casing 95 is proximally attached to the proximal hollow end portion 8' of the catheter 1'. When needle 21 is fully inserted into the catheter 1' (and duckbill valve casing 95 is proximally attached to the proximal hollow end portion 8'), the proximal portion of duckbill valve casing 95 is thus in contact with the distal portion of hub 22.

According to one embodiment (not shown) the downward grip 15 is not connected to the hub (5, 5') but to the duckbill valve casing 95 thus fixing forward arm (10, 10', 110) to the duckbill valve casing 95. The grasping arms 15a and 15b are adapted to connect around the duckbill valve casing 95, preferably a snap-on tube clip connection wherein downward grip 15 snaps on duckbill valve casing 95. Thus the catheter (1, 1', 1") moves distally/proximally in accordance with the forward arm (10, 10', 110) due to the fact that the cannula 2 is connected to the hub (5, 5') which is attached to proximal hollow end portion (8, 8', 8") which is connected (via luer connection) to duckbill valve casing 95.

The duckbill valve casing 95 length is usually between 5 mm and 10 mm. Its diameter is usually between 2 mm and 6 mm. A puncturing needle with such duckbill valve casing 95 can be used with the catheter closing unit 60 and the IV catheter 1" and forward arm 110, put all together.

According to another embodiment of the present invention the duck bill valve is fully incased in the hollow portion of proximal end portion 8'.

According to another embodiment of the present invention, the system comprises a needle unit 200, as shown in FIGS. 11A-11E. The needle unit comprises a proximal hub 205 attached proximally to the needle 21. The proximal hub 205 comprises a stopper 85' and longitudinal cylindrical protrusions 90' in the same manner as end portion 8''' comprises stopper 85 and longitudinal cylindrical protrusions 90, with the same sizes, materials, etc., mutatis mutandis. Thus the catheter closing unit 60 is configured to be mounted on the needle unit 200 (in a similar manner as on end portion 8''') and fixed thereto for insertion of the catheter. The needle unit 200 is connected to IV catheter 1' (explained hereinabove) end portion 8' in a luer connection at the distal portion of hub 205. The needle unit 200 passes through catheter 2, protrudes therefrom and is ready for insertion.

Figure 11A:
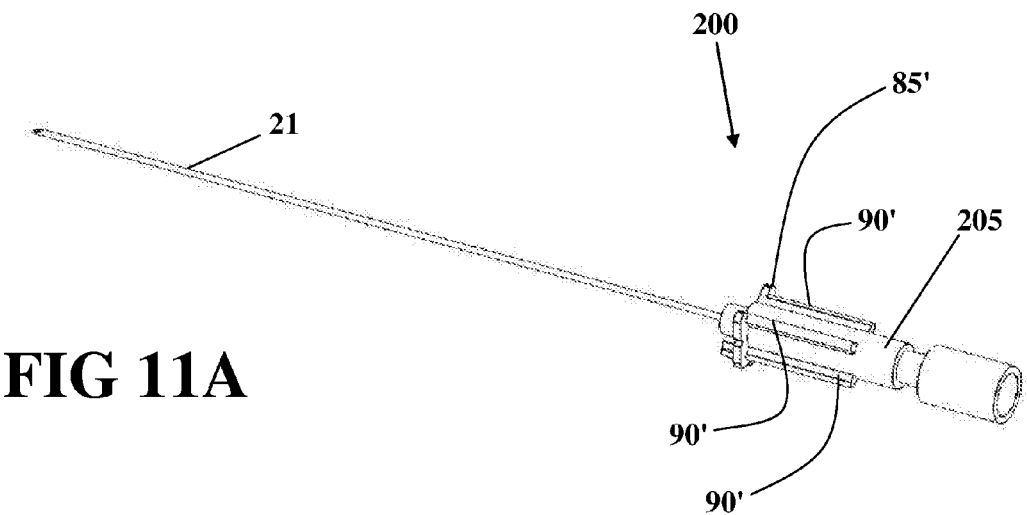
FIGS. 11A-11E illustrate perspective views of an embodiment relating to a needle unit.
Figure 11B:
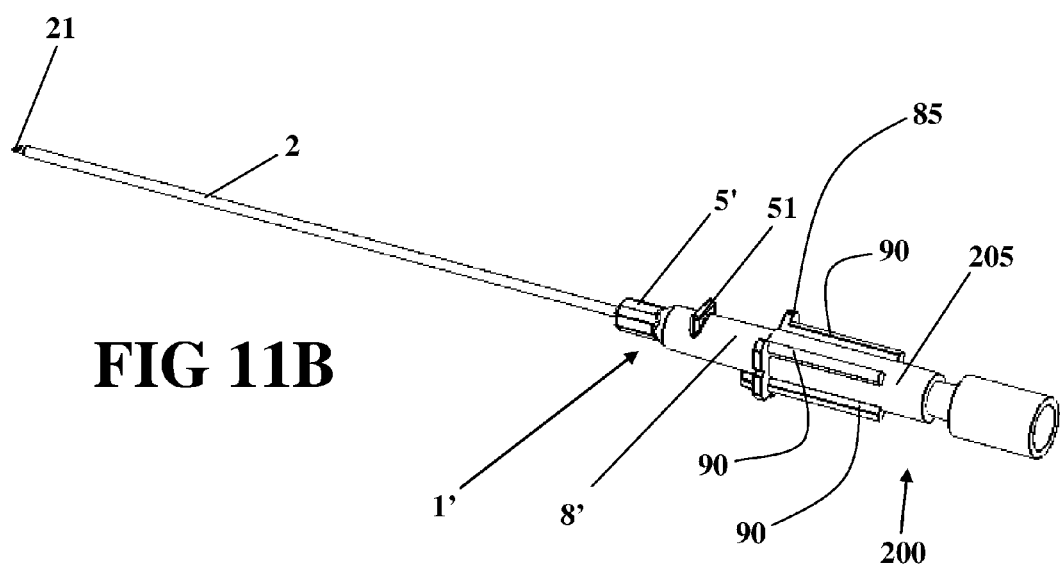
Figure 11C:
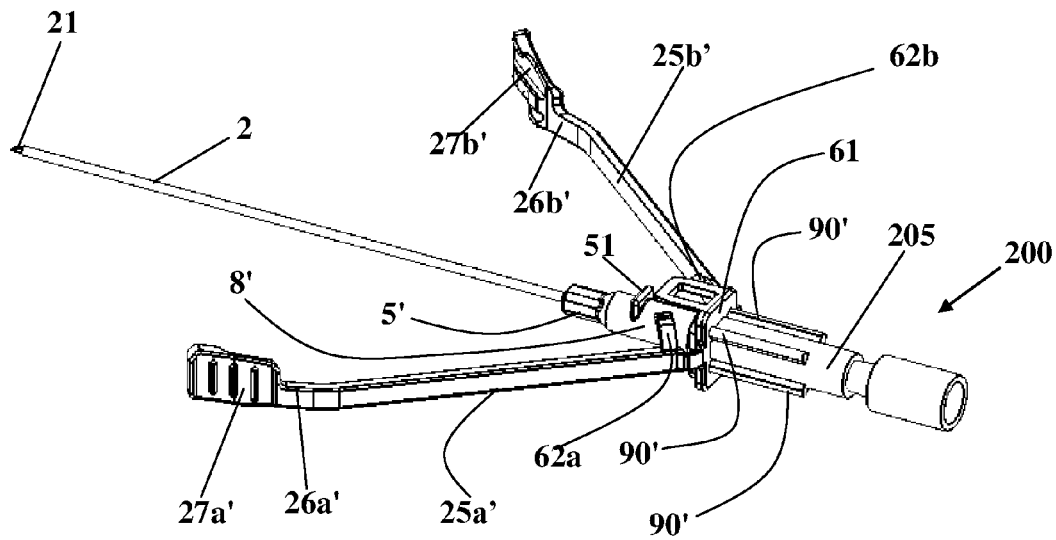
Figure 11D:
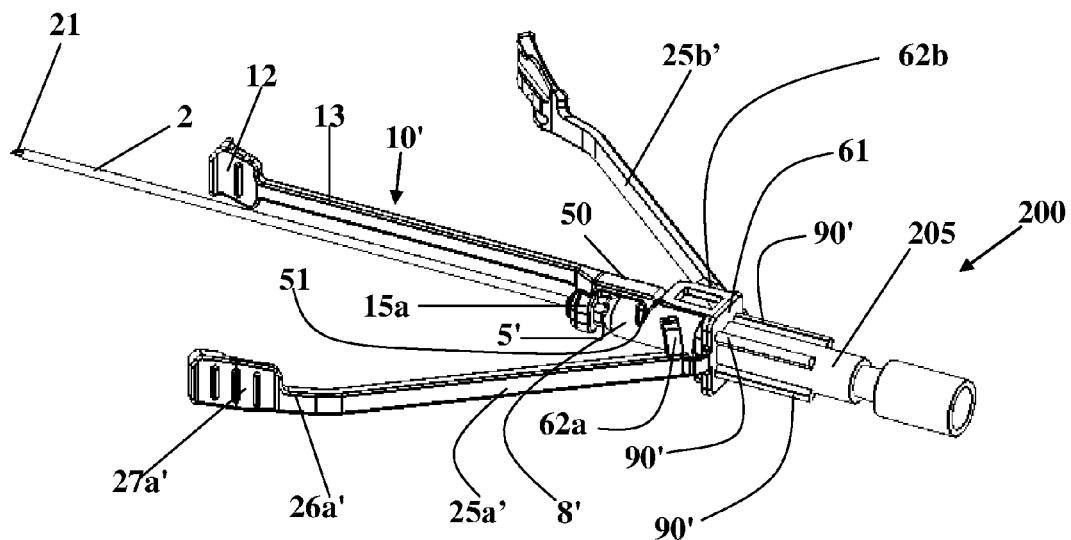
Figure 11E:
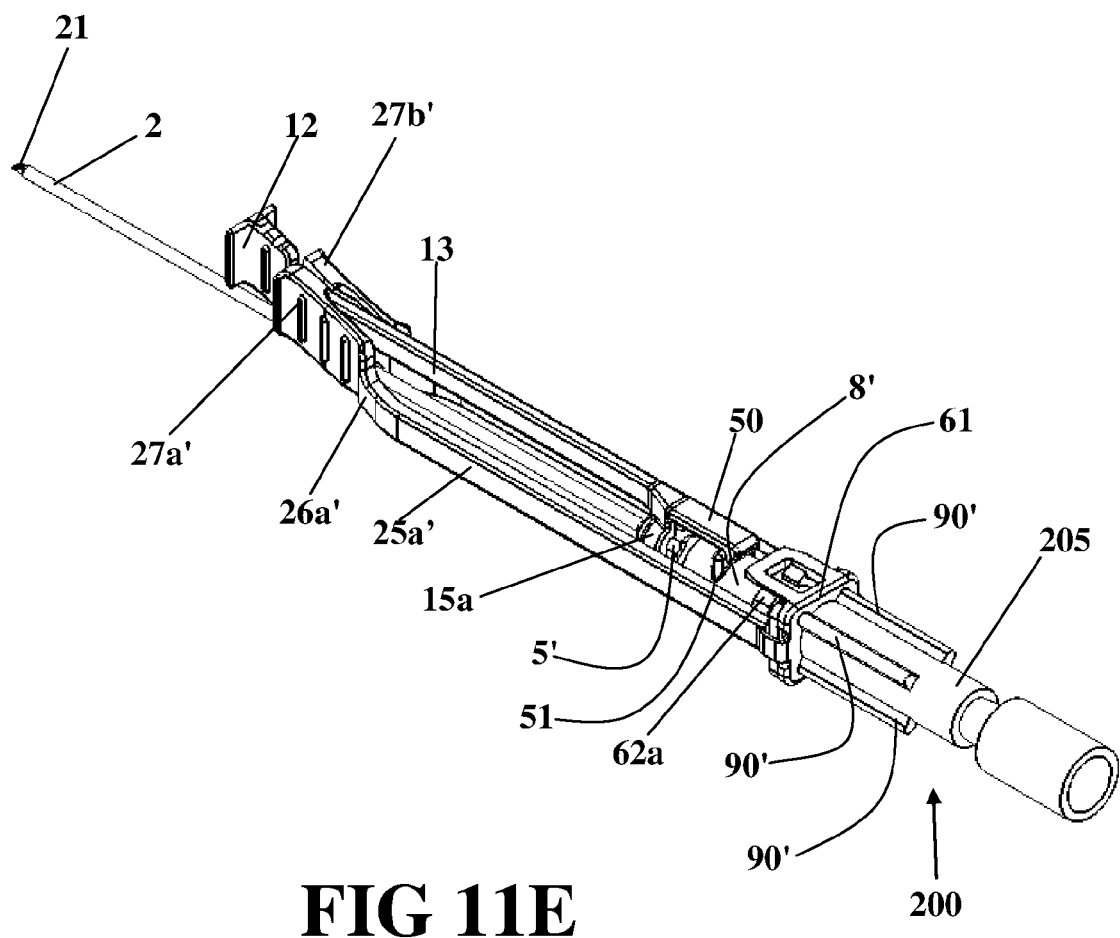

FIG. 11A shows the needle unit 200 alone. FIG. 11B shows the needle unit 200 inserted in the IV catheter 1'. FIG. 11C shows the needle unit 200 inserted in the IV catheter 1' and with the catheter closing unit 60 mounted thereon. FIGS. 11D-11E show the needle unit 200 inserted in the IV catheter 1' and with the catheter closing unit 60 mounted thereon and with the forward arm 10' attached to the IV catheter 1'.

The needle unit 200 inserted in the IV catheter 1' with the catheter closing unit 60 mounted thereon and with the forward arm 10' attached to the IV catheter 1', is grasped by the medical personnel user. The skin is punctured by the needle 21 and forward arm 10' moved distally inserting IV cannula 2 of catheter 1' (in a similar manner as explained hereinabove). After the cannula 2 is fully inserted, the luer connection between needle unit 200 and end portion 8' is disconnected followed by the proximal retrieval of needle unit 200 with catheter closing unit 60 still mounted on it. Then the distal arm 10' is disconnected from IV catheter 1' and the IV catheter 1' (hub/end portion) is fixed to the skin of the patient. Optionally the catheter closing unit 60 can be proximally slid and retrieved prior to the needle unit 200 retrieval. Optionally the distal arm 10' can be disconnected at a one of the aforementioned stages after the cannula 2 has been fully inserted.

Distal arm 110 could also be used with this embodiment. The distal portion of the hub of needle unit 200 can also be attached to safety capsule 90 or duckbill valve casing 95 (them being connected to end portion 8'), mutatis mutandis.

The present invention is especially advantageous because it comprises at least two grasping points/areas (for the fingers to grasp) configured to perform maneuvering of the cannula 2 (e.g. the distal maneuvering for the insertion). One grasping point is the proximal grasping point (used in prior art devices). The proximal grasping point can be one or more of the following elements: catheter end portion (e.g. 8, 8', 8"), catheter hubs (e.g. 5, 5'), the valve 7, wings 6a and 6b, or anything connected/attached to these elements. The other grasping point is the distal grasping point which is the forward arm (preferably the forward arm grip 12). A user could also use one of the grasping points for maneuvering and then switch to the other (and optionally switch back etc.).

In some cases, the proximal grasping point can be a proximal portion of the needle or anything proximally attached to the needle. This can be efficient especially for the puncturing stage. Such proximal grasping point can be a proximal portion of needle holder unit 20, proximal hub 205, etc.

According to an embodiment of the present invention the system is constructed such that the cannula 2 and needle 21 passing therethrough, are in a position elevated in height from the height of the bottom of side arms 25*a* and 25*b* of needle holder unit 20. Preferably, the cannula 2 (and needle 21 passing therethrough) is positioned in height substantially parallel to the middle height line of arms 25*a* and 25*b* (e.g. FIG. 5B). This elevated feature provides additional protection to the cannula 2 and prevents it from touching portions of the patient's skin, what could cause needles contamination. Thus the needle holder unit 20 is constructed such that the needle 21 extending from the hub 22 extends in a position elevated from the bottom of side arms 25*a* and 25*b*. The location of hollow passage 29 is compatible accordingly. The connection of end portion 8 to hub 22 is also accordingly.

In a similar manner the connection of catheter closing unit 60 to the IV catheter 1″ is constructed such that the cannula 2 is in a position elevated in height from the height of the bottom of side arms 25*a*' and 25*b*' of catheter closing unit 60.

In a similar manner the connection of catheter closing unit 60 to proximal hub 205 of needle unit 200 is constructed such that the needle 21 is in a position elevated in height from the height of the bottom of side arms 25*a*' and 25*b*' of catheter closing unit 60. The connection of end portion 8' (of catheter 1') to proximal hub 205, is also accordingly.

The present invention also relates to a method for insertion of an IV catheter into a blood vessel of a patient in connection with the device explained hereinabove in accordance with all the embodiments (and all combinations thereof). Portions of the method were explained hereinabove.

The present invention also relates to a method for inserting an IV catheter into a blood vessel of a patient comprising the steps of:
  A) providing a needle passing through said IV catheter, puncturing the patient's blood vessel;
  B) providing a forward arm attachably connected to a proximal portion of said IV catheter or element connected thereto and extending distally therefrom, pulling/pushing said forward arm distally thus inserting the cannula into the blood vessel;
  C) inserting the cannula in place by continuing to pull/push the forward arm distally;
  D) proximally pulling the puncturing needle until it exits the IV catheter;
  E) Disconnecting the forward arm from said IV catheter or element connected thereto;
  F) fixing the IV catheter to the patient's skin.

Preferably the method is executed with the needle holder unit or the catheter closing unit as explained hereinabove. The needle holder unit or the catheter closing unit is pulled proximally along with the needle in step C.

According to the embodiment with the needle holder unit, the method step D is done by proximally pulling the needle holder unit.

According to the embodiment with the liftable gripper 50 and flat protrusion 51, the method step E comprises lifting the liftable griper for releasing the forward arm.

According to the embodiment with the catheter closing unit, the method comprises proximally pulling the catheter closing unit and removing it from the IV catheter after step D.

According to the embodiment with the flexible forward arm (or forward arm 110 with the middle section comprising portion 113*a* and flexible portion 113*b*), the method step C further comprises lifting the distal portion of the forward arm upwards.

According to one embodiment, the method steps B and C are done by a user's finger of the hand grasping the catheter insertion system.

According to one embodiment, the method step C is done by the hand not grasping the insertion system.

According to the embodiment with the system with the needle unit 200 (FIGS. 11A-11E), step D is done by proximally pulling the needle unit 200.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:
1. A catheter insertion system comprising:
  a. an IV catheter comprising a distal cannula attached to a proximal hollow hub;
  b. a forward arm attachably connected to a proximal portion of said IV catheter or element connected thereto, and extending distally therefrom;
  c. a needle configured to pass through and protrude from the cannula;
  wherein the forward arm comprises a distal forward grip;
  wherein the forward arm comprises a middle section connecting between the distal forward grip and a downward grip connected to the proximal end of said middle section,
  wherein said downward grip comprises two grasping arms extending downwards and substantially curved.

2. The catheter insertion system according to claim 1, wherein the middle section comprises a distal portion connected to the forward grip and a thinner proximal portion connected to the downward grip, wherein the thinner proximal portion is flexible.

3. A catheter insertion system comprising:
  a. an IV catheter comprising a distal cannula attached to a proximal hollow hub;
  b. a forward arm attachably connected to a proximal portion of said IV catheter or element connected thereto, and extending distally therefrom;
  a needle configured to pass through and protrude from the cannula;
  wherein the forward arm comprises a proximal liftable gripper; and the IV catheter comprises a proximal hollow end portion comprising a flat protrusion,
  wherein the proximal liftable gripper comprises a proximal protrusion extending downwards with a distal flat portion adapted to grip and be placed at the proximal side of said flat protrusion.

4. A catheter insertion system comprising:
  a. an IV catheter comprising a distal cannula attached to a proximal hollow hub;

b. a forward arm attachably connected to a proximal portion of said IV catheter or element connected thereto, and extending distally therefrom;

c. a needle configured to pass through and protrude from the cannula;

said system further comprising a needle holder unit comprising the needle and two side arms substantially parallel to said needle;

wherein the needle holder unit comprises a proximal hub, wherein the needle is distally connected to said proximal hub; and wherein the needle holder unit two side arms are connected to the proximal hub at their proximal ends;

wherein the two side arms comprise slanted portions at their distal ends, such that said distal ends are disposed near to each other.

5. The catheter insertion system according to claim 4, wherein the side arms are configured to open outwardly when the catheter hub and/or downward grip engage the slanted portions.

6. A catheter insertion system comprising:

a. an IV catheter comprising a distal cannula attached to a proximal hollow hub;

b. a forward arm attachably connected to a proximal portion of said IV catheter or element connected thereto, and extending distally therefrom;

c. a needle configured to pass through and protrude from the cannula;

wherein the IV catheter comprises a proximal hollow end portion; and wherein the system further comprises a safety capsule, wherein the needle is freely slidable in relation to said safety capsule, wherein said safety capsule automatically senses the end of the needle and instantly locks out to fully encapsulate the distal needle tip of the needle, wherein said safety capsule is proximally attached to the proximal hollow end portion in a luer connection.

7. The catheter insertion system according to claim 6, wherein the forward arm comprises a distal forward grip;

wherein the forward arm comprises a middle section connecting between the distal forward grip and a downward grip connected to the proximal end of said middle section, wherein said downward grip comprises two grasping arms extending downwards and substantially curved; and wherein the forward arm is attachably connected to the safety capsule by means of the downward grip thus fixing said forward arm to said safety capsule.

8. A catheter insertion system comprising:

a. an IV catheter with a distal cannula attached to a proximal hollow hub, and comprising a proximal hollow end portion;

b. a forward arm attachably connected to a proximal portion of said IV catheter or element connected thereto, and extending distally therefrom;

c. a catheter closing unit comprising a proximal stabilizing grip which comprises a hollow surface corresponding in shape and adapted to be close fitting around said proximal end portion;

said catheter closing unit further comprises two side arms attached to said proximal stabilizing grip.

9. The catheter insertion system according to claim 8, wherein the forward arm comprises a distal forward grip;

wherein the forward arm comprises a middle section connecting between the distal forward grip and a downward grip connected to the proximal end of said middle section, wherein said downward grip comprises two grasping arms extending downwards and substantially curved;

wherein the side arms are configures to open outwardly when the catheter proximal hub and/or downward grip engage the slanted portions.

10. A catheter insertion system comprising:

a. an IV catheter with a distal cannula attached to a proximal hollow hub, and comprising a proximal hollow end portion;

b. a forward arm attachably connected to a proximal portion of said IV catheter or element connected thereto, and extending distally therefrom;

c. a needle unit comprising a needle distally attached to a proximal hub, said needle unit hub optionally comprising a stopper;

d. a catheter closing unit comprising a proximal stabilizing grip which comprises a hollow surface corresponding in shape and adapted to be close fitting around said needle unit proximal hub;

said catheter closing unit further comprises two side arms attached to said proximal stabilizing grip;

wherein the needle unit hub distal portion is configured to connect in a luer connection to the proximal end of the proximal hollow end portion.

11. A catheter closing unit comprising a proximal stabilizing grip which comprises a hollow surface corresponding in shape and adapted to be close fitting around a needle unit hub or a catheter hub or proximal end portion;

wherein said catheter closing unit comprises two side arms attached to said proximal stabilizing grip;

wherein the two side arms comprise slanted portions at their distal ends, such that said distal ends are disposed near to each other;

wherein the portions of the two side arms proximal to the slanted portions are generally straight and parallel to each other;

wherein the slanted portions are connected to forward finger grips at their distal ends;

wherein the forward finger grips are substantially parallel to each other.

12. A method for inserting an IV catheter into a blood vessel of a patient comprising the steps of:

providing a catheter insertion system comprising:

a. an IV catheter comprising a distal cannula attached to a proximal hollow hub;

b. a forward arm attachably connected to a proximal portion of said IV catheter or element connected thereto, and extending distally therefrom;

c. a needle passing through said IV catheter and protruding from the cannula, wherein the forward arm comprises a proximal liftable gripper; and the IV catheter comprises a proximal hollow end portion comprising a flat protrusion, wherein the proximal liftable gripper comprises a proximal protrusion extending downwards with a distal flat portion adapted to grip and be placed at the proximal side of said flat protrusion, A) puncturing the patient's blood vessel;

B) pulling/pushing said forward arm distally thus inserting the cannula into the blood vessel;

C) inserting the cannula in place by continuing to pull/push the forward arm distally;

D) proximally pulling a puncturing needle until it exits the IV catheter;

E) disconnecting the forward arm from said IV catheter or element connected thereto;
F) fixing the IV catheter to the patient's skin;
wherein step E comprises lifting the liftable griper for releasing the forward arm.

13. A method for inserting an IV catheter into a blood vessel of a patient comprising the steps of:
providing a catheter insertion system comprising:
a. an IV catheter comprising a distal cannula attached to a proximal hollow hub, and comprising a proximal hollow end portion;
b. a forward arm attachably connected to a proximal portion of said IV catheter or element connected thereto, and extending distally therefrom;
c. a needle passing through said IV catheter;
d. a catheter closing unit comprising a proximal stabilizing grip which comprises a hollow surface corresponding in shape and adapted to be close fitting around said proximal end portion;
wherein said catheter closing unit further comprises two side arms attached to said proximal stabilizing grip,
A) puncturing the patient's blood vessel;
B) pulling/pushing said forward arm distally thus inserting the cannula into the blood vessel;
C) inserting the cannula in place by continuing to pull/push the forward arm distally;
D) proximally pulling a puncturing needle until it exits the IV catheter;
E) disconnecting the forward arm from said IV catheter or element connected thereto;
F) fixing the IV catheter to the patient's skin;
proximally pulling the catheter closing unit and removing it from the IV catheter after step D.

14. A method for inserting an IV catheter into a blood vessel of a patient comprising the steps of:
providing a catheter insertion system comprising:
a. an IV catheter comprising a distal cannula attached to a proximal hollow hub;
b. a forward arm attachably connected to a proximal portion of said IV catheter or element connected thereto, and extending distally therefrom;
c. a needle passing through said IV catheter and protruding from the cannula, wherein
the forward arm comprises a distal forward grip,
the forward arm comprises a middle section connecting between the distal forward grip and a downward grip connected to the proximal end of said middle section,
said downward grip comprises two grasping arms extending downwards and substantially curved,
the middle section comprises a distal portion connected to the forward grip and a thinner proximal portion connected to the downward grip, wherein
the thinner proximal portion is flexible,
A) puncturing the patient's blood vessel;
B) pulling/pushing said forward arm distally thus inserting the cannula into the blood vessel;
C) inserting the cannula in place by continuing to pull/push the forward arm distally;
D) proximally pulling a puncturing needle until it exits the IV catheter;
E) disconnecting the forward arm from said IV catheter or element connected thereto;
F) fixing the IV catheter to the patient's skin;
wherein step C further comprises lifting the distal portion of the forward arm upwards.

* * * * *